(12) United States Patent
Handy et al.

(10) Patent No.: US 7,074,175 B2
(45) Date of Patent: Jul. 11, 2006

(54) THERMOTHERAPY VIA TARGETED DELIVERY OF NANOSCALE MAGNETIC PARTICLES

(76) Inventors: Erik Schroeder Handy, 56 Milton St., Arlington, MA (US) 02474; Robert Ivkov, 39 Lincoln Ave., Marblehead, MA (US) 01945; Diane Ellis-Busby, 875 Brockelman Rd., Lancaster, MA (US) 01523; Allan Foreman, 2 Pawnee La., Epping, NH (US) 03042

( * ) Notice: Subject to any disclaimer, the term of this patent is extended or adjusted under 35 U.S.C. 154(b) by 510 days.

(21) Appl. No.: 10/176,950

(22) Filed: Jun. 18, 2002

(65) Prior Publication Data

US 2003/0028071 A1 Feb. 6, 2003

Related U.S. Application Data

(60) Provisional application No. 60/307,785, filed on Jul. 25, 2001.

(51) Int. Cl.
*A61N 2/00* (2006.01)

(52) U.S. Cl. ..................... 600/9; 977/DIG. 1

(58) Field of Classification Search .......... 600/9–15; 607/103, 105; 424/422–423, 426, 428, 430, 424/434–437, 489–491, 493–502, 647–648, 424/1.29, 1.33, 1.53, 9.32–9.323; 977/DIG. 1
See application file for complete search history.

(56) References Cited

U.S. PATENT DOCUMENTS

| | | |
|---|---|---|
| 4,106,488 A | 8/1978 | Gordon |
| 4,303,636 A | 12/1981 | Gordon |
| 4,312,364 A | 1/1982 | Convert |
| 4,323,056 A | 4/1982 | Borrelli |
| 4,392,040 A | 7/1983 | Rand |
| 4,452,773 A | 6/1984 | Molday |
| 4,454,234 A | 6/1984 | Czerlinski |
| 4,545,368 A | 10/1985 | Rand et al. |
| RE32,066 E | 1/1986 | Leveen |
| 4,569,836 A | 2/1986 | Gordon |
| 4,574,782 A | 3/1986 | Borrelli et al. |
| 4,590,922 A | 5/1986 | Gordon |
| 4,610,241 A | 9/1986 | Gordon |
| 4,622,952 A | 11/1986 | Gordon |
| 4,662,359 A | 5/1987 | Gordon |
| 4,678,667 A | 7/1987 | Meares |
| 4,708,718 A | 11/1987 | Daniels |
| 4,735,796 A | 4/1988 | Gordon |
| 4,753,894 A | 6/1988 | Frankel |
| 4,758,429 A | 7/1988 | Gordon |
| 4,767,611 A | 8/1988 | Gordon |

(Continued)

FOREIGN PATENT DOCUMENTS

EP   0040512 A   11/1981

(Continued)

OTHER PUBLICATIONS

International Search Report for PCT/US02/23650.

(Continued)

*Primary Examiner*—John P. Lacyk
(74) *Attorney, Agent, or Firm*—Raymond A. Miller; Pepper Hamilton LLP; Lucy Elandjian

(57) ABSTRACT

Disclosed are compositions comprising magnetic nanoparticles, a biocompatible coating, and a target-specific ligand. Also disclosed are devices for treating diseased tissue for use with such compositions. Further disclosed are methods for treating diseased tissue, such as cancer, using such compositions and devices, as well as methods for treating diseased tissue utilizing hypertermia.

58 Claims, 7 Drawing Sheets

U.S. PATENT DOCUMENTS

| | | |
|---|---|---|
| 4,813,399 A | 3/1989 | Gordon |
| 4,889,120 A | 12/1989 | Gordon |
| 4,923,437 A | 5/1990 | Gordon |
| 4,950,221 A | 8/1990 | Gordon |
| 4,983,159 A | 1/1991 | Rand |
| 4,996,991 A | 3/1991 | Gordon |
| 5,043,101 A | 8/1991 | Gordon |
| 5,067,952 A | 11/1991 | Gudov et al. |
| 5,087,438 A | 2/1992 | Gordon |
| 5,099,756 A | 3/1992 | Franconi |
| 5,128,147 A | 7/1992 | Leveen |
| 5,169,774 A | 12/1992 | Frankel |
| 5,203,782 A | 4/1993 | Gudov |
| 5,300,750 A | 4/1994 | Carter, Jr. et al. |
| 5,411,730 A | 5/1995 | Kirpotin |
| 5,441,746 A | 8/1995 | Chagnon |
| 5,468,210 A | 11/1995 | Matsui |
| 5,506,343 A | 4/1996 | Kufe |
| 5,547,682 A | 8/1996 | Chagnon |
| 5,612,019 A | 3/1997 | Gordon |
| 5,620,480 A | 4/1997 | Rudie |
| 5,622,686 A | 4/1997 | Gordon |
| 5,629,197 A | 5/1997 | Ring |
| 5,658,234 A | 8/1997 | Dunlavy |
| 5,667,171 A | 9/1997 | Fowell |
| 5,705,157 A | 1/1998 | Greene |
| 5,720,954 A | 2/1998 | Hudziak |
| 5,772,997 A | 6/1998 | Hudziak |
| 5,859,206 A | 1/1999 | Vandlen |
| 5,891,996 A | 4/1999 | Mateo de Acosta del Rio |
| 5,916,539 A | 6/1999 | Pilgrimm |
| 5,922,845 A | 7/1999 | Deo |
| 5,935,866 A | 8/1999 | Chagnon |
| 5,958,374 A | 9/1999 | Meares |
| 5,968,511 A | 10/1999 | Akita |
| 6,008,203 A | 12/1999 | Magnani |
| 6,015,567 A | 1/2000 | Hudziak |
| 6,037,129 A | 3/2000 | Cole |
| 6,054,561 A | 4/2000 | Ring |
| 6,074,337 A | 6/2000 | Tucker |
| 6,149,576 A | 11/2000 | Gray |
| 6,165,440 A | 12/2000 | Esenaliev |
| 6,165,464 A | 12/2000 | Hudziak |
| 6,167,313 A | 12/2000 | Gray |
| 6,190,870 B1 | 2/2001 | Schmitz |
| 6,242,196 B1 | 6/2001 | Spiegelman |
| 6,252,050 B1 | 6/2001 | Ashkenazi |
| 6,281,202 B1 | 8/2001 | Magnani |
| 6,303,755 B1 | 10/2001 | Deo |
| 6,344,203 B1 | 2/2002 | Sandrin |
| 6,347,633 B1 | 2/2002 | Groth |
| 6,387,371 B1 | 5/2002 | Hudziak |
| 6,387,888 B1 | 5/2002 | Mincheff |
| 6,391,026 B1 | 5/2002 | Hung |
| 6,541,039 B1 * | 4/2003 | Lesniak et al. ............. 424/647 |
| 2002/0052594 A1 | 5/2002 | Goldenberg |

FOREIGN PATENT DOCUMENTS

| | | |
|---|---|---|
| EP | 0136530 | 4/1985 |
| EP | 0333381 A2 | 9/1989 |
| EP | 0400940 A2 | 12/1990 |
| EP | 0543498 A1 | 5/1993 |
| EP | 0913167 A2 | 5/1999 |
| EP | 0673255 B1 | 8/2001 |
| JP | 1244767 | 9/1989 |
| WO | WO9411023 | 5/1994 |
| WO | 00344270/EP B1 | 11/1994 |
| WO | WO 97/43005 | 11/1997 |
| WO | WO 99/19000 | 4/1999 |
| WO | WO 00/52714 A2 | 9/2000 |
| WO | WO 01/500 A1 | 2/2001 |
| WO | WO 01/501 A1 | 2/2001 |
| WO | WO 01/17611 A1 | 3/2001 |
| WO | WO 01/37721 A2 | 5/2001 |

OTHER PUBLICATIONS

Jordan et al., Magnetic Fluid Hyperthermia (MFH), *Science and Clinical Applications of Magnetic Carriers*, 1997, pp. 569-595.

Peasley, K. W. "Destruction of human immunodeficiency-infected cells by ferrofluid particles manipulated by an external magnetic field: mechanical disruption and selective introduction of cytotoxic or antiretroviral substances into target cells." Medical Hypotheses, 1996, pp. 5-12, vol. 46, No. 1, England (ABSTRACT).

Torchilin, V.P., et al. "Magnetic sephadex as a carrier for enzyme immobilization and drug targeting." Journal of Biomedical Materials Research, 1985, pp. 461-466, vol. 19, No. 4, United States (ABSTRACT).

Molina, M.A., et al. "Trastuzumab (herceptin), a humanized anti-Her2 receptor monoclonal antibody, inhibits basal and activated Her2 ectodomain cleavage in breast cancer cells." Cancer Research 2001, pp. 4744-4749, Jun. 15;61(12) (ABSTRACT).

Wong, C., et al. "Human scFv antibody fragments specific for the epithelial tumour marker MUC-1, selected by phage display on living cells." Cancer Immunol. Immunother. 2001, pp. 93-101, Apr.;50(2). (ABSTRACT).

Winthrop, M.D., et al. "Development of a hyperimmune anti-MUC-1 single chain antibody fragment phage display library for targeting breast cancer." Clinical Cancer Research 1999, pp. 3088-3094, Oct.;5(10 suppl.) (ABSTRACT).

Richman, C.M., et al. "Systemic radiotherapy in metastatic breast cancer using 90Y-linked monoclonal MUC-1 antibodies." Crit Rev Oncol Hematol 2001, pp. 25-35, vol. 38, Ireland (ABSTRACT).

Kobayashi, T., et al. "Targeting hyperthermia for renal cell carcinoma using human MN antigen-specific magnetoliposomes". Japanese Journal of Cancer Research 2001 vol. 92 No. 10 (ABSTRACT).

Young, A.J., et al. "A pulsed power supply system for producing high intensity magnetic and electric fields for medical applications". IEEE Conference Record—Abstracts. PPPS-2001 Pulsed Power Plasma Science 2001. 28th IEEE International Conference on Plasma Science and 13th IEEE International Conference on Plasma Science and 13th IEEE International Pulsed Power Conference (cat. No. 01ch37255) 2001, pp. 322 USA (ABSTRACT).

Peterson, J.A., "Effect of multiple, repeated doses of radioimmunotherapy on target antigen expression (breast MUC-1 mucin) in breast carcinomas", Cancer Res. 1997, pp. 1103-1108, vol. 57(6), (ABSTRACT).

Diaz, A.K., et al. "Expression of epithelial mucians Mucl, Muc2, and Muc3 in ductal carcinoma in situ of the breast", Breast J. 2001, pp. 40-45, vol. 7(1), (ABSTRACT).

Barratt-Boyles, S.M. "Making the most of mucin: a novel target for tumor immunotherapy", Cancer Immunol. Immunother, 1996, pp. 142-151, vol. 43(3), (ABSTRACT).

Menard, S.M., et al. "Role of Her2 gene overexpression in breast carcinoma", Cell Physiol. 2000, pp. 150-162, vol. 182(2), (ABSTRACT).

Hadden, J.W., "The immunology and immunotherapy of breast cancer: an update", Int. J. Immunopharacol. 1999, pp. 79-101, vol. 21(2), (ABSTRACT).

Tucker, R.D., et al. "Defining the heating characteristics of ferromagnetic implants using calorimetry" J. of Biomedical Materials Research, 2000, vol. 53, pp. 791-798.(ABSTRACT).

Takegami, K., et al. "New ferromagnetic bone cement for local hyperthermia" J. Biomedical Materials Research, 1998, vol. 43, pp. 210-214. .(ABSTRACT).

Paulus, J.A., et al. "Corrosion analysis of NiCu and PdCo thermal seed alloys used as interstitial hyperthermia implants", 1997, vol. 18, pp. 1609-1614. .(ABSTRACT).

Graef, G.L. "Materials for low Curie temperature induction heating of tumors (Hyperthermia)" Ph.D. Dissertation, University of Arizona, 1991. . (ABSTRACT).

Petrarca, C. et al. "Isolation of Muc1-primed B lymphocyted from tumour-draining lymph nodes by immunomagnetic beads". Cancer Immunology Immunotherapy 1999 pp. 272-277 vol. 47 No. 5 (ABSTRACT).

Shinkai, M., et al. "Targeting hyperthermia for renal call carcinoma human mn antigen-specific magnetoliposomes" Jpn. J. Cancer Res., 2001, vol. 92, pp. 1138-1145. (ABSTRACT).

Suzuki, M., et al. "Preparation and characteristics of magnetite-labelled antibody with the use of poly(ethylene glycol) derivatives". Biotechnol Appl. Biochem., 1995, vol. 21, pp. 335-345.

Shinkai, M., et al. "Anti-conjugated magnetoliposomes for targeting cancer cells and their application in hyperthermia". Biotechnol Appl Biochem 1994 vol. 21, pp. 125-137.

Jordan, A., et al. "Magnetic fluid hyperthermia (MFH): Cancer treatment with AC magnetic field induced excitation of biocompatible superparamagnetic nanoparticles". J. Magnetism and Magnetic Materials 1999, pp. 413-419, vol. 201.

Jordan, A., et al. "Inductive heating of ferromagnetic particles and magnetic fluids: physical evaluation of their potential for hyperthermia". Int. J. Hyperthermia 1993, pp. 51-68, vol. 9.

Jordan, A., et al. "Magnetic Fluid Hyperthermia (MFH)", in *Scientific and Clinical Applications of Magnetic Carriers*, Hafeli et al., eds. 1997, pp. 569-595, USA.

Chan, D.C.F., et al. "Synthesis and evaluation of colloidal magnetic iron oxides for the site-specific radiofrequency-induced hyperthermia of cancer", J. Magnetism and Magnetic Materials, 1993, pp. 374-378, vol. 122, Holland.

Brusentsov, N.A., et al. "Evaluation of ferromagnetic fluids and suspensions for the site-specific radiofrequency-induced hyperthermia of MX11 sarcoma cells in vitro" J. Magnetism and Magnetic Materials, 2001, vol. 225, 113-117.

Jones, S.K., et al. "Experimental examination of a targeted hyperthermia system using inductively heated ferromagnetic microspheres in rabbit kidney" Physics in Medicine and Biology, 2001, vol. 46, pp. 385-398.

Jones, S.K., et al. "Evaluation of ferromagnetic materials for low-frequency hysteresis heating of tumors" Physics in Medicine and Biology, 1992, vol. 37, pp. 293-299.

Moroz, P., et al. "Targeting liver tumors with hyperthermia: Ferromagnetic embolization in a rabbit liver tumor model" J. of Surgical Oncology, 2001, vol. 78, pp. 22-29.

Hiergeist, R., et al. "Application of magnetic ferrofluids for hyperthermia" J. Magnetism and Magnetic Materials, 1999, vol. 201, pp. 420-422.

Shinkai, M., et al."Intracellular hyperthermia for cancer using magnetite cationic liposomes: In vitro study" Jpn. J. Cancer Research, 1996, vol. 87, pp. 1179-1183.

Carter, P., "Improving the efficacy of antibody-based cancer therapies", Nature Reviews 2001, pp. 118-129, vol. 1.

McDevitt, M., et al. "Tumor therapy with targeted atomic nanogenerators", Science 2001, pp. 1537-1550, vol. 294.

Segal, D.M., et al. "Introduction: bispecific antibodies", J. Immunol. Methods 2001, pp. 1-6, vol. 248.

Reiter, Y., et al. "Recombinant immunotoxins in targeted cancer cell therapy", Adv. Cancer Res. 2001, pp. 93-124.

Hergt, R.W.T., et al."Physical limits of hyperthermia using magnetite fine particles" IEEE Trans. On Mag., 1998, vol. 34, pp. 3745-3754.

Hynynen, K., et al. "State of the art in medicine: Hyperthermia in cancer treatment" Investigative Radiology, 1990, vol. 2, 824-834.

Jordan, A., et al. "Cellular uptake of magnetic fluid particles and their effects on human adenocarcinoma cells exposed to AC magnetic fields in vitro" Int. J. Hyperthermia, 1996, vol. 12, pp. 705-722.

Chan, D.C.F., et al. "Physical chemistry and in vivo tissue heating properites of colloidal magnetic iron oxides with increased power adsorption rates" in *Scientific and Clinical Applications of Magnetic Carriers*, Hafeli et al., eds. 1997, pp. 607-618, Plenum Press, New York, USA.

Suzuki, S. et al. "Studies on liposomal ferromagnetic particles and a technique of high frequency inductive heating" Jpn. J. Soc. Cancer Ther., 1990, vol. 25, pp. 2649-2658.

Gordon, R.T., et al. "Intracellular hyperthermia: a biophysical approach to cancer treatment via intracellular temperature and biophysical alterations" Medical Hypothesis, 1979, vol. 5, pp. 83-102.

Goldin, J.H., et al. "The effects od diapulse on the healing of wounds: a double-blind randomized controlled trial in man" Brit. J. of Plastic Surgery, 1981, vol. 34, pp. 267-270.

Gilchrist, R.K., et al. "Selective inductive heating of lymph nodes" Annals of Surgery, 1957, vol. 146, pp. 596-606.

Luderer, A.A., et al. "Glass-ceramic-mediated, magnetic-field-induced localized hyperthermia: Response of a murine mammary carcinoma" Radiation Research, 1983, vol. 94, pp. 190-198.

Bartlett, K., et al. "On the use of ferromagnetic microparticles in microwave and radio frequency hyperthermia" J. of the Inst. of Electronic and Radio Engineers, 1998, vol. 58, pp. 197-201.

Bacri, J.C., et al. "Use of magnetic nanoparticles for thermolysis of cells in a ferrofluid" in *Scientific and Clinical Applications of Magnetic Carriers*, Hafeli et al., eds. 1997, pp. 597-606, Plenum Press, New York, USA.

Mitsumori, M., et al. "Targeted hyperthermia using dextran magnetite complex: A new treatment modality for liver tumors" Hepato-Gastroenterology, 1996, vol. 43, pp. 1431-1437.

Borrelli, N.F., et al. "Hysteresis heating for the treatment of tumors". Phys Med Biol. 1984, pp. 487-494, vol. 29, No. 5, England.

Mitsumori, M., et al. "Development of intra-arterial hyperthermia using a dextran-magnetite complex" Int. J. Hyperthermia, 1994, vol. 10, pp. 785-793.

* cited by examiner

THERMOTHERAPY VIA TARGETED DELIVERY OF NANOSCALE MAGNETIC PARTICLES

CROSS REFERENCE TO RELATED APPLICATION

This is a non-provisional application claiming the benefit of and priority to provisional patent application No. 60/307,785 filed on Jul. 25, 2001.

TECHNICAL FIELD

The present invention relates generally to thermotherapy, more specifically, to magnetic material compositions, devices for use with magnetic material compositions, and methods related thereto for thermotherapy via targeted delivery of nanoscale magnetic particles.

BACKGROUND

Despite considerable research effort and some success, cancer is still the second leading cause of death in the United States, claiming more than 500,000 lives each year according to American Cancer Society estimates. Traditional treatments are either invasive or expose the patient to considerable toxicity with often only modest success. Early detection, a result of better diagnostic practices and technology has improved the prognosis for many patients. Nevertheless, some cancers defy currently available treatment options, despite these improvements. Of the many forms of cancer that still pose a medical challenge, prostate, breast, lung, and liver claim the vast majority of lives each year.

Breast cancer is the most common cancer in women, with well over 100,000 new cases being diagnosed each year in the United States alone. Breast cancer usually begins in the cells lining a breast duct, the eventual invasion of these cells outside the ductal environment presenting the risk of metastases. Later stages of breast cancer are fatal and typically have advanced to a point in which cancer cells have invaded the lymphatic system, and may include other organs such as the liver, bone, lungs, and brain.

Conventional treatments for breast cancer, both in late and early stages, typically include surgery followed by radiation and/or chemotherapy. These techniques are not always effective, and even if effective, they suffer from certain deficiencies. Surgical procedures include complete removal of the breast and removal of only the tumor (lumpectomy). In early stage cancer, complete removal of the breast provides the best assurance against recurrence, but is disfiguring and requires the patient to make a very difficult choice. Lumpectomy is less disfiguring, but is associated with a greater risk of recurrence. Radiation and chemotherapy are arduous and are not completely effective against recurrence.

For these reasons, it was desirable to provide improved and alternative techniques for treating breast cancer. Such techniques should be less invasive and traumatic to the patient than the present techniques, should result in minimum or no disfigurement of the breast, and should be effective locally within target sites of the breast and other diseased organs. Preferably, the techniques should be capable of being performed in a single or very few treatment session(s), with minimal toxicity to the patient. In addition, the diseased tissues should be targeted by the treatment without requiring significant operator skill and input.

Immunotherapy is a rapidly expanding type of therapy used for treating a variety of human diseases including cancer. The FDA has approved a number of antibody-based cancer therapeutics. The emergence of antibody therapies is made possible by important advances in antibody technologies. The ability to engineer antibodies, fragments, and peptides with altered properties such as antigen binding affinity, molecular architecture, specificity, and valence has enhanced their use in therapies. The advantages of antibody engineering have overcome the limitations of mouse monoclonal antibodies. Cancer immunotherapeutics have made use of advances in the chimerization and humanization of mouse antibodies to reduce immunogenic responses in humans. High affinity human antibodies have also been obtained from transgenic mice that contain many human immunoglobulin genes. In addition, phage display technology, ribosome display, and DNA shuffling have allowed for the discovery of antibody fragments and peptides that have the desirable properties of high affinity and low immunogenicity for use as targeting ligands. All of these advances have made it possible to design an immunotherapy that has a desired antigen binding affinity, specificity, and minimal immune response.

The field of cancer immunotherapy makes use of markers that are expressed or over-expressed on cancer cells in comparison to normal cells. The identification of such markers is ongoing and the choice of a ligand/marker combination is critical to the success of any immunotherapy. Immunotherapy has fallen into several classes: (1) antibodies themselves that target growth receptors, disrupt cytokine pathways, or induce complement or antibody-dependent cytotoxicity; (2) direct arming of an antibody with a toxin, a radionucleotide, or a cytokine; (3) indirect arming of an antibody by attachment to immunoliposomes used to deliver a toxin or by attachment to an immunological cell effector (bispecific antibodies). Although armed antibodies have shown more potent tumor activity in clinical trials, there have been unacceptably high levels of toxicity. The disadvantage of therapies that rely on delivery of immunotoxins or radionucleotides (direct and indirect arming) has been that these agents are active at all times. There have been problems with damage to non-tumor cells and toxicity issues along with delivery challenges. Many immunotherapies have faced challenges with shed markers and delivery to the intended target. Cancer cells commonly shed antigen targets into the blood stream. Many antibody-based therapies are diluted by interaction with shed antigens. In addition, immune complexes can be formed between the immunotherapeutic and the shed antigen, which can lead to dose-limiting toxicities.

Generation of heat in a range of about 40° C. to about 46° C. (hyperthermia) can cause irreversible damage to diseased cells, whereas normal cells are not similarly affected. Diseased tissue may be treated by elevating the temperature of the individual cells contained within to a lethal level (cellular thermotherapy) using a suitable magnetic material confined to the vicinity of the cell and induction heating the material using an alternating magnetic field (AMF).

Hyperthermia may hold promise as a treatment for cancer because it induces instantaneous necrosis (typically called thermo-ablation) and/or a heat-shock response in cells (classical hyperthermia), leading to cell death via a series of biochemical changes within the cell. State-of-the-art systems that employ radio-frequency (RF) hyperthermia, such as annular phased array systems (APAS), attempt to tune E-field energy for regional heating of deep-seated tumors. Such techniques are limited by the heterogeneities of tissue electrical conductivities and that of highly perfused tissues, leading to the unsolved problems of 'hot spot' phenomena in unintended tissues with concomitant underdosage in the desired areas. These factors make selective heating of specific regions with such E-field dominant systems very difficult.

Another strategy that utilizes RF hyperthermia requires surgical implantation of microwave- or RF-antennae or self-regulating thermal seeds. In addition to its invasiveness, this approach provides only limited (if any) treatment options for metastases because it requires knowledge of the precise location of the tumor, and is thus incapable of targeting undetected individual cancer cells or cell clusters not immediately adjacent to the primary tumor site. Clinical outcomes of these techniques are limited by problems with deposition of physical power to the desired tumor tissues.

Hyperthermia for cancer treatment using colloidal single domain magnetic suspensions (i.e., magnetic fluids) exposed to RF fields has been recognized for several decades. However, a major problem with magnetic fluid hyperthermia has been the inability to selectively deliver a lethal dose of particles to the tumor cells.

SUMMARY OF THE INVENTION

In view of the above, there is a need for a hyperthermia based treatment method for diseased tissue, such as cancer, that incorporates selective delivery of magnetic fields to the diseased tissue. It is also desirable to have methods for treating diseased tissue, such as cancer, in a safe and effective manner, with minimal invasion, and short treatment periods.

It is, therefore, an object of the present invention to formulate magnetic material compositions including nanoscale magnetic particles and target-specific ligands useful in the treatment of diseased tissue, such as cancer.

It is another object of the present invention to provide a device for the treatment of diseased tissue that is capable of providing an alternating magnetic field.

It is yet another object of the present invention to provide a method that utilizes compositions of nanoscale magnetic materials and target-specific ligands in conjunction with a device that provides alternating magnetic fields to treat diseased tissue by killing diseased cells via hyperthermia.

It is a further object of the present invention to provide methods for the treatment of diseased tissue, such as cancer, in a safe and effective manner, with minimal invasion, and short treatment periods.

The present invention pertains to magnetic material compositions that include magnetic particles forming a single magnetic domain; a biocompatible coating material for the particle; and a ligand that is selective to at least one cancer marker, and that can be bound to an uncoated portion of the particle, bound to a coated portion of the particle, bound to the particle and partially covered by the coating, or intercalated into the coating. The present invention also pertains to devices for treating cancer by interacting with magnetic particles targeted to cancer cells in a patient. Such a device includes a magnetic generator having a core defining at least part of a magnetic circuit, two poles of the core defining a gap therebetween, a magnetic field passing between two poles, the gap being of sufficient size to receive a portion of the patient containing the cancer cells; and a power supply coupled to provide energy to the magnetic generator so that the magnetic field passing between the two poles alternates at a frequency of about 1 kHz or more.

The present invention further pertains to methods related to such magnetic material compositions and devices for the treatment of cancer. One such method includes the administration to the patient of a magnetic material composition that includes at least one, single domain, magnetic particle attached to a cancer-cell specific ligand, and application of an alternating magnetic field to a region of the patient containing the cancer so as to inductively heat the magnetic material composition and kill the cancer cells.

The therapeutic methods of the present invention provide for the treatment of diseased tissue, such as cancer, in a safe and effective manner, with minimal invasion, and short treatment periods.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
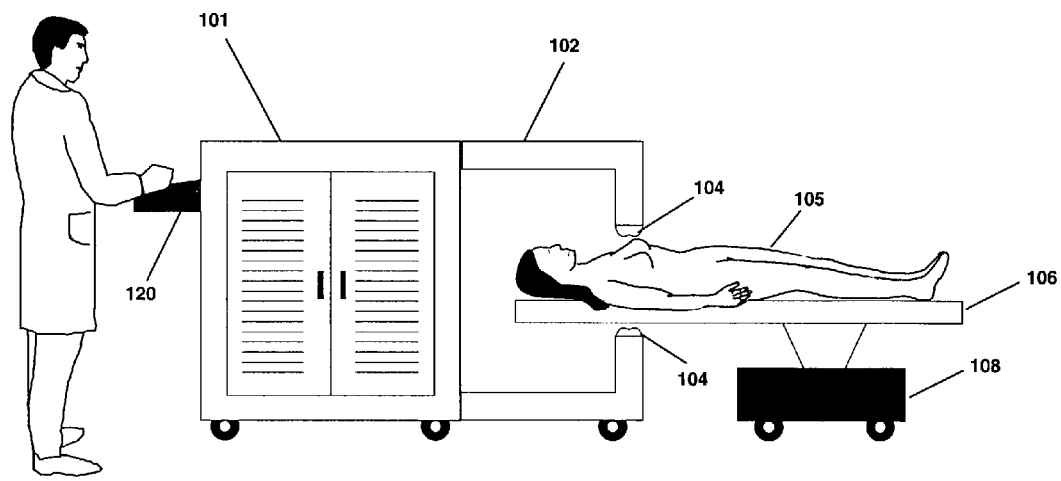
FIG. 1 schematically illustrates a thermotherapy treatment system according to an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention pertains to magnetic material compositions, devices for treating diseased tissue for use with magnetic material compositions, and methods for treating diseased tissue utilizing such devices and magnetic material compositions. The therapeutic methods disclosed herein include the targeted delivery of nanometer sized magnetic particles to diseased tissue. Specifically, the present invention pertains to such compositions, devices, and methods for the treatment of cancer. The term "bioprobe", as used herein, refers to the composition including a magnetic particle, a biocompatible coating material, and a target-specific ligand. The term "ligand", as used herein, refers to compounds which target biological markers. Examples of ligands include proteins, peptides, antibodies, antibody fragments, saccharides, carbohydrates, glycans, cytokines, chemokines, nucleotides, lectins, lipids, receptors, steroids, neurotransmitters, Cluster Designation/Differentiation (CD) markers, imprinted polymers, and the like. The methods for treating diseased tissue disclosed herein include administering to a patient the bioprobes suspended in an appropriate medium, and applying, via a device capable of interacting with the bioprobes, an alternating magnetic field to an area of the patient containing the bioprobes to heat the bioprobes sufficiently to kill cancerous cells.

One embodiment of the invention, as illustrated in FIG. 1, includes an alternating magnetic field (AMF) generator located within a cabinet 101 designed to produce an alternating magnetic field (AMF) that may be guided to a specific location within a patient 105 by a magnetic circuit 102. The therapeutic methods of the present invention may be performed following a diagnosis or evaluation of cancer or a pre-cancerous condition or other disease in one or more areas of the patient. Specifically, the diagnosed disease may be breast cancer or metastatic breast cancer. The manner of making the diagnosis does not form part of the invention and may be performed using any standard method. However, the present invention, or aspects thereof, may be amenable to a diagnostic function alone or in conjunction with another method or apparatus. The patient lies upon an X-Y horizontal and vertical axis positioning bed 106. The bed 106 is both horizontally and vertically positionable via a bed controller 108. The AMF generator produces an AMF in the magnetic circuit 102 that exits the magnetic circuit at one pole face 104, passing through the air gap and the desired treatment area of the patient, and reenters the circuit through the opposing pole face 104, thus completing the circuit. An operator or medical technician is able to both control and monitor the AMF characteristics and bed positioning via the control panel 120.

Figure 2:
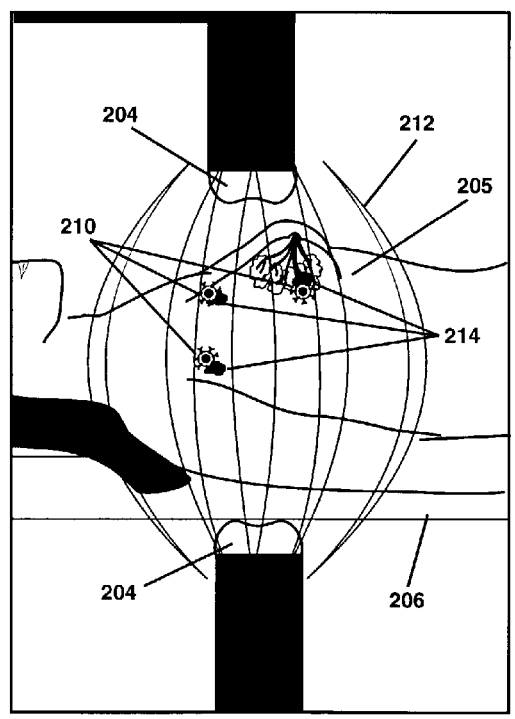
FIG. 2 schematically illustrates a thermotherapy treatment according to an embodiment of the present invention.

FIG. 2 illustrates a treatment of a patient with a device for treating cancer according to an embodiment of the present invention. The diseased or cancerous treatment area 205 of the patient is localized in the region between the magnetic poles 204 via the positionable bed 206. This region may be the breast, an area in close proximity to the breast, lymph nodes and ducts, liver, lung, bones, or any other site or region of metastasis. An AMF may be applied to the treatment area 205 of the patient, as illustrated by the magnetic lines of flux 212. The magnetic field, manifested by the magnetic lines of flux 212 interacts with both healthy and diseased tissue in the localized area. Bioprobes 210, containing at least one appropriate ligand selective to the particular type of cancer, are bound to cancer cells 214. In the illustrated case, the bioprobes 210 are selective to breast cancer. The bioprobes 210 become excited by interacting with the applied AMF and are inductively heated to a temperature sufficient to kill diseased or cancerous cells. Heat generated in the excited bioprobes 210 passes to the cancer cells, thereby causing the cancer cells to die.

It will be appreciated that other types of cancers may be treated using the device, for example, lung, prostate and the like. Furthermore, the poles 204 may be formed from pieces whose gap is adjustable, so as to permit other parts of the body to be treated. It is advantageous to set the gap between the poles 204 to be sufficiently large to permit the part of the body containing the cancer to enter the gap, but not be so large as to reduce the magnetic field strength.

Figure 3:
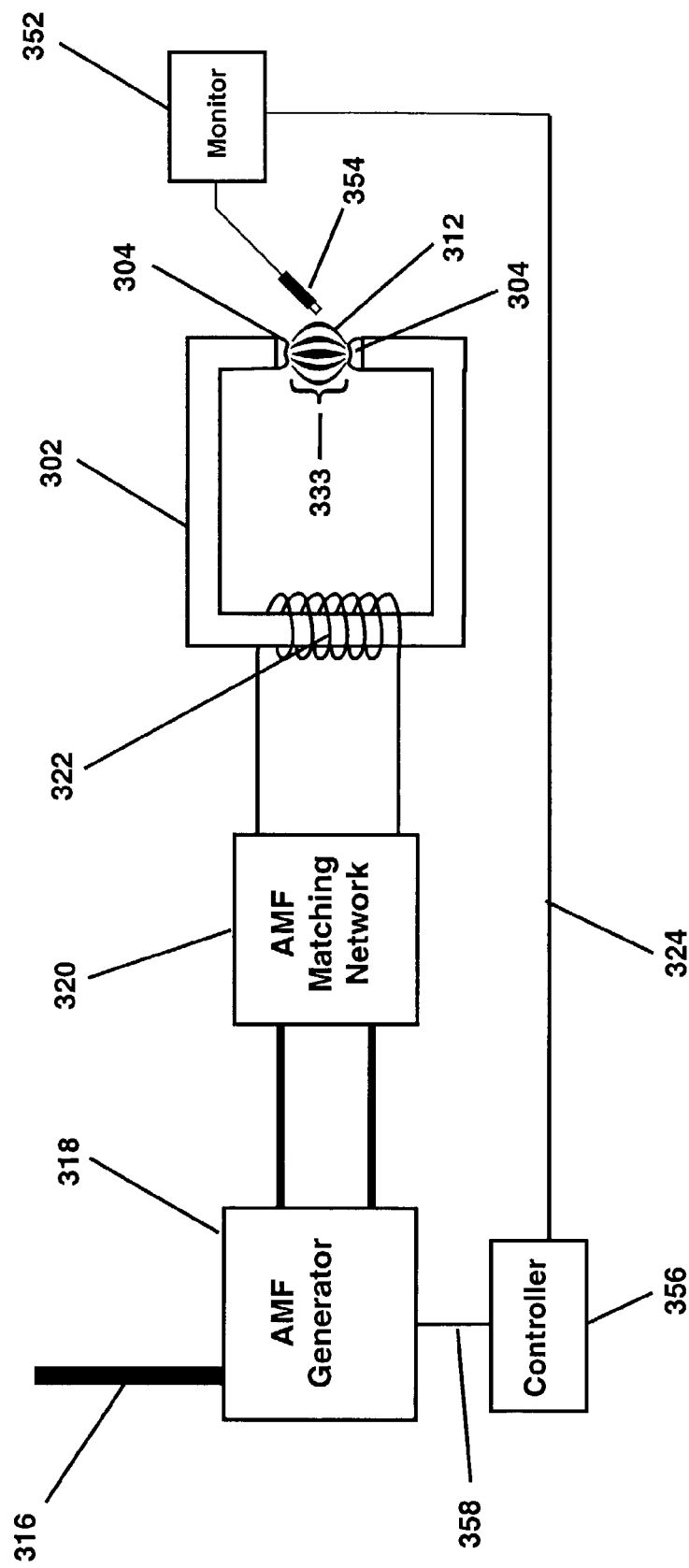
FIG. 3 schematically illustrates a circuit for producing a thermotherapeutic alternating magnetic field according to an embodiment of the present invention.

FIG. 3 illustrates a circuit for producing an AMF according to an embodiment of the present invention. The AMF generator 318 is supplied with alternating current (AC) power via the conduit 316. A circulating fluid supply is also provided in the conduit 316. The AMF generator 318 may become hot, and it may be cooled with the circulating fluid supply while in operation. The fluid may be water; however a fluid such as silicone oil or other inorganic or organic (carbon based) fluids with suitable thermal and electric properties may be preferable. Such a fluid increases generator efficiency. The energy produced by the generator 318 is directed through the AMF matching network 320 where the impedance of the generator is matched to the impedance of the coil 322. The impedance of the AMF matching network 320 may be adjustable to minimize the energy reflected back to the generator 318. In another embodiment, the generator frequency may be automatically adjusted to minimize the reflected energy. The modified energy may be directed to the magnetic circuit 302. An AMF is induced in the magnetic circuit 302 as a result of the current passing through the solenoid coil 322. Magnetic lines of flux 312 are produced in the gap 333 between the poles 304 in the magnetic circuit 302. A feedback loop 324 may be provided for monitoring the magnetic field profile in the gap 333 between the poles 304. A suitable probe 354 provides data to the monitor 352, which relays information to the controller 356 via an appropriate data bus 324. Information from the controller 356 is relayed to the generator 318 via an appropriate data bus 358. Monitoring the magnetic field profile may be useful in detecting the presence of magnetic particles, monitoring an inductance of tissue, and monitoring the temperature of tissue located in the gap 333.

Figure 4A:
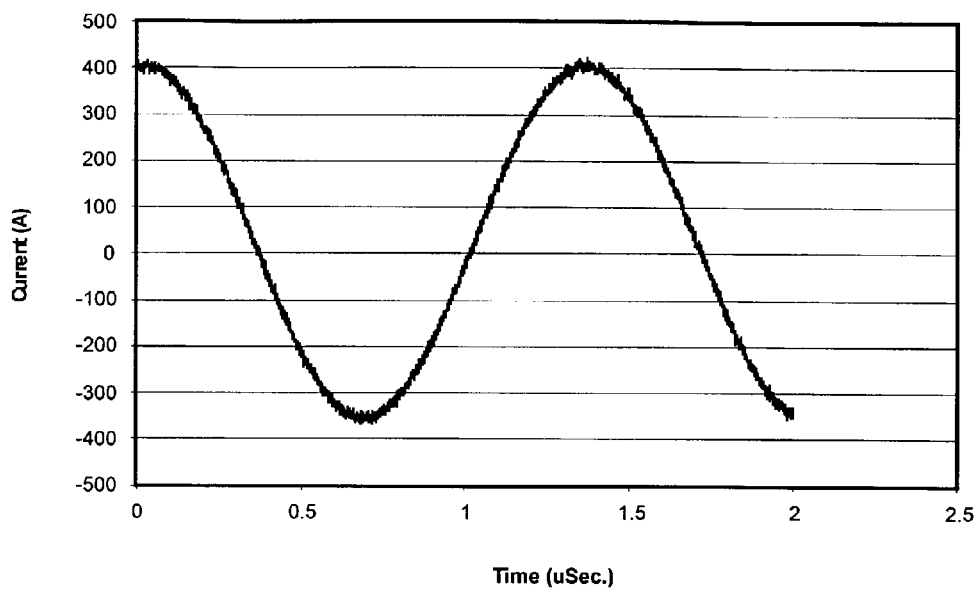
FIG. 4a graphically illustrates a thermotherapeutic sinusoidal current waveform according to an embodiment of the present invention.
Figure 4B:
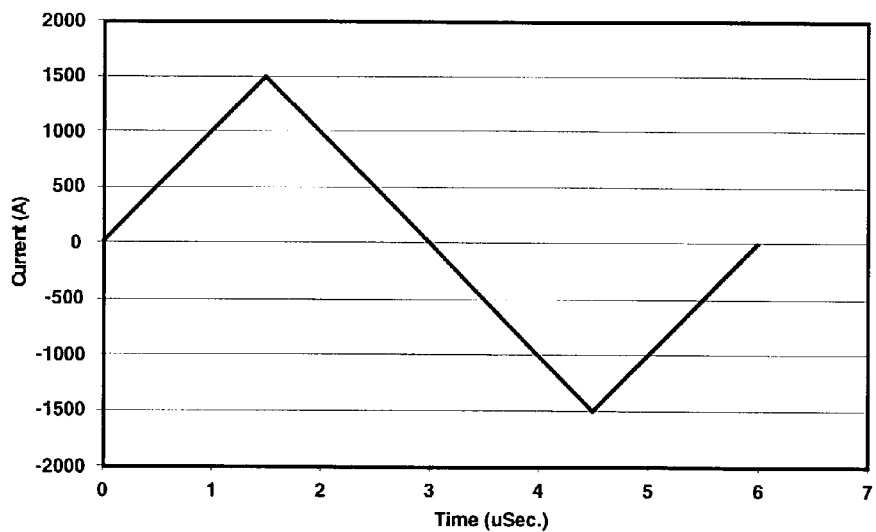
FIG. 4b graphically illustrates a thermotherapeutic triangular current waveform according to an embodiment of the present invention.

Measuring alternating magnetic fields directly is extremely difficult. Because the AMF is proportional to the current in the coil 322, characteristics of the AMF may be defined in terms of the coil current, which can readily be measured with available test equipment. For example, the coil current may be viewed and measured with a calibrated Rogowski coil and any oscilloscope of suitable bandwidth. The fundamental waveform may be observed as the direct measure of the magnitude and direction of the coil current. Many different types of fundamental waveforms may be used for the AMF. For example, FIG. 4a illustrates a sinusoidal current waveform, and FIG. 4b illustrates a triangular current waveform. The shape of the fundamental waveform may also be square, sawtooth, or trapezoidal.

Most practical generators produce an approximation of these waveforms with some amount of distortion. In most applications, this waveform may be nearly symmetrical around zero, as illustrated in FIGS. 4a and 4b. However, there may be a static (or DC) current superimposed on the waveform (DC offset). FIGS. 4a and 4b show at least one cycle of two different fundamental waveforms with zero or near zero DC offsets. The fundamental period may be defined as the time it takes to complete one cycle. The fundamental frequency may be defined as the reciprocal of the fundamental period. The fundamental frequency may be between 1 kHz and 1 GHz, preferably between 50 kHz and 15 MHz, and more preferably between 100 kHz and 500 kHz. The fundamental frequency may be intentionally modulated (as in many high-resolution RADAR designs), and may often vary slightly as a result of imperfections in the RF generator design.

Figure 5A:
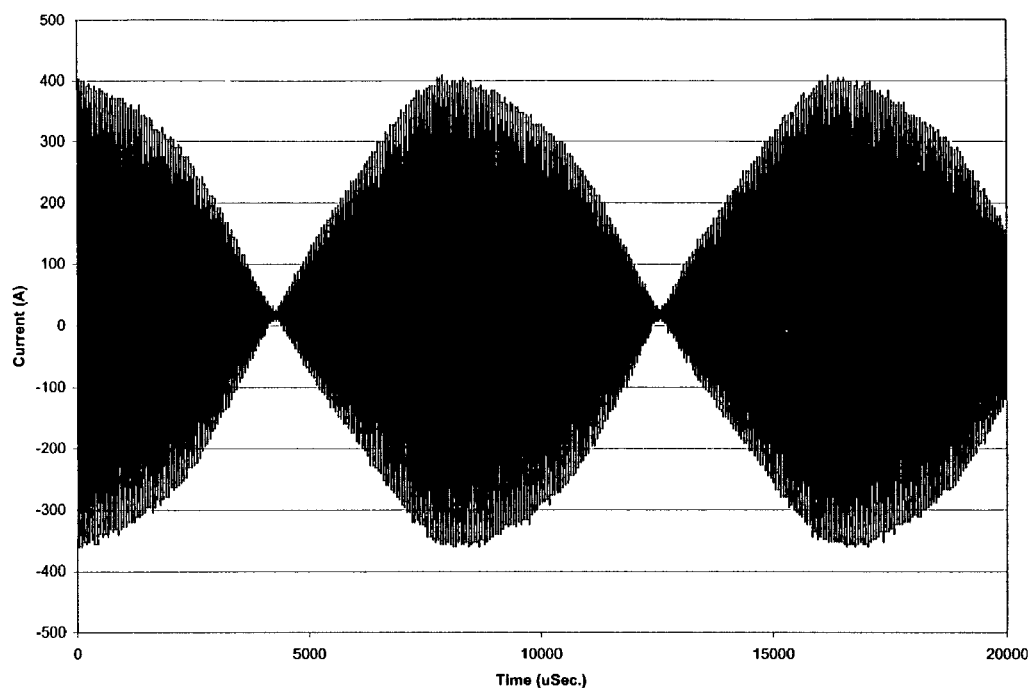
FIG. 5a graphically illustrates a thermotherapeutic sinusoidal waveform modulation according to an embodiment of the present invention.
Figure 5B:
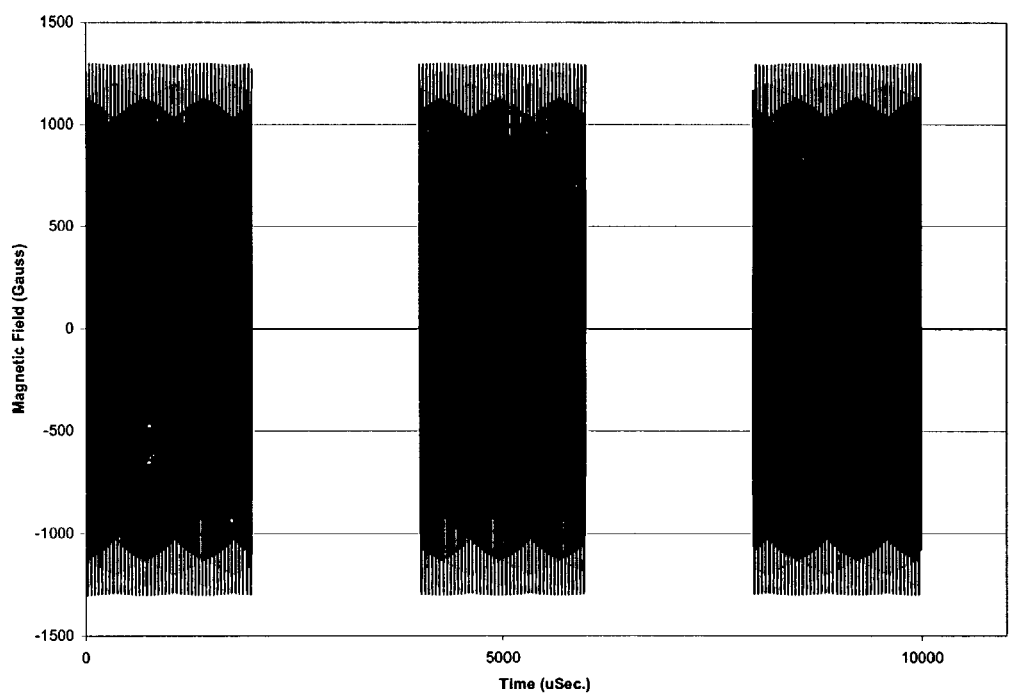
FIG. 5b graphically illustrates a thermotherapeutic pulsed waveform modulation according to an embodiment of the present invention.

The amplitude of the waveform may also be modulated. FIG. 5a illustrates an embodiment in which a sinusoidal current modulation envelope may be used, and FIG. 5b illustrates an embodiment that utilizes a square modulation envelope. The shape of the amplitude modulation envelope may typically be sinusoidal, square, triangular, trapezoidal or sawtooth, and may be any variation or combination thereof, or may be some other shape.

The AMF produced by the generator may also be pulsed. Pulse width is traditionally defined as the time between the −3 dBc points of the output of a square law crystal detector. Because this measurement technique is cumbersome in this application, we use an alternate definition of pulse width. For the purpose of this invention, pulse width may be defined as the time interval between the 50% amplitude point of the pulse envelope leading edge and the 50% amplitude point of the pulse envelope trailing edge. The pulse width may also be modulated.

The pulse repetition frequency (PRF) is defined as the number of times per second that the amplitude modulation envelope is repeated. The PRF typically lies between 0.0017 Hz and 1000 MHz. The PRF may also be modulated. The duty cycle may be defined as the product of the pulse width and the PRF, and thus is dimensionless. In order to be defined as pulsed, the duty of the generator 318 must be less than unity (or 100%).

The AMF may be constrained to prevent heating healthy tissue to lethal temperatures (typically $\geq 43°$ C.). This may be accomplished in a variety of ways.

The peak amplitude of the AMF may be adjusted.

The PRF may be adjusted.

The pulse width may be adjusted.

The fundamental frequency may be adjusted.

These four characteristics may be adjusted to maximize heating rate of the bioprobes and, simultaneously, to minimize the heating rate of the healthy tissue located within the treatment volume. These conditions may vary depending upon tissue types to be treated, thus the operator may determine efficacious operation levels. In one embodiment, one or more of these characteristics may be adjusted during treatment based upon one or more continuously monitored physical characteristics of tissue in the treatment volume by the probe 354, such as temperature or impedance. This information may then be supplied as input to the generator 318, via the monitor 352, the data bus 324, the controller 356, and the data bus 358 to control output, constituting the feedback loop. The generator output may be adjusted so that the peak AMF strength is between about 10 and about 10,000 Oersteds (Oe). Preferably, the peak AMF strength is between about 20 and about 3000 Oe, and more preferably, between about 100 and about 2000 Oe.

In another embodiment of the present invention, the differential heating of the bioprobes, as compared to that of the healthy tissue, may be maximized. The bioprobes 210 heat in response to each cycle of the AMF. Assuming the fundamental frequency, the PRF, and the pulse width remain constant, the heat output of the bioprobe 210 will continue to increase as peak amplitude of the AMF increases until the magnetic material of the bioprobe reaches saturation. Beyond this point, additional increases in AMF amplitude yield almost no additional heating. At AMF amplitudes below saturation however, it can be said that bioprobe heating is a function of AMF amplitude. Unlike bioprobes, healthy tissue heating is a result of eddy current flow and a function of the rate of change of the AMF. In particular, the eddy current and resultant tissue heating following the expressions:

$$I_{eddy} \propto dB/dT \tag{1}$$

$$\text{Tissue Heating} \propto I_{eddy}^2 \tag{2}$$

From the relationships (1) and (2), it is evident that reducing the rate of change of the AMF yields a significant reduction in tissue heating. In one embodiment of the present invention, this relationship is exploited by using a symmetrical triangular wave, as shown in FIG. 4b, as the fundamental waveform. By avoiding the high rates of change as a sinusoid crosses the X-axis (FIG. 4a), and substituting the constant but lower rate of change associated with a triangular waveform (FIG. 4b), tissue heating may be reduced with little or no sacrifice in bioprobe heating. A triangular waveform, as shown in FIG. 4b, may be achieved by using an appropriate generator, such as a linear amplifier-based generator. Some distortion of the triangle is inevitable, but tangible reductions in tissue heating result from even small reductions in dB/dT.

The heating of both the tissue and the bioprobes increase with increased AMF amplitude. At low AMF amplitudes, small increases yield significant increases in magnetic heating. As the bioprobes approach saturation however, their relationship with the AMF amplitude becomes one of diminishing return. This relationship is unique to the particular magnetic material, as are the values that constitute "low" or "saturating" AMF amplitudes. Bioprobe heating is at first related to the AMF amplitude by an exponent >1, which gradually diminishes to an exponent <1 as saturation is approached. At typical pulse widths and duty cycles, eddy current heating is directly related to duty cycle. The capability to pulse the generator output, as illustrated in FIGS. 5a or 5b, allows the benefits of operating at higher AMF amplitudes while maintaining a constant reduced tissue heating by reducing the duty cycle.

It is desirable to apply the AMF to the treatment area 205 of the patient 105. Generating high peak amplitude AMF over a large area requires a very large AMF generator and exposes large amounts of healthy tissue to unnecessary eddy current heating. Without some means of directing the field to where it is useful, disease in the chest or trunk could only be practically treated by placing the patient within a large solenoid coil. This would expose most of the major organs to eddy current heating, which must then be monitored and the AMF adjusted so as not to overheat any part of a variety of tissue types. Each of these tissue types has a different rate of eddy current heating. The peak AMF strength would need to be reduced to protect those tissue types that experience the most extreme eddy current heating. If the varieties of exposed tissue are minimized, it is likely that the AMF strength can be increased, and thereby reducing the treatment time and increasing the efficacy. One method of confining the high peak amplitude AMF to treatment area 205 is by defining the lowest reluctance path of magnetic flux with high permeability magnetic material. This path is referred to as a magnetic circuit (102 in FIG. 1 and 302 in FIG. 3). The magnetic circuit may be provided so that all or most of the magnetic flux produced by the coil 322 may be directed to the treatment area 205. One benefit of the magnetic circuit 302 is that the necessary amount of flux may be reduced since the amount of flux extending beyond the treatment area 205 is minimized. Reducing the required flux reduces the required size and power of the AMF generator, and minimizes exposure of tissue outside the treatment area 205 to high peak amplitude AMF. In addition, a reduced area of AMF exposure avoids the unintentional heating of surgical or dental implants and reduces the likelihood that they will need to be removed prior to treatment, thereby avoiding invasive medical procedures. Concentrating the field permits the treatment of large volumes within the chest or trunk with a portable size device.

The material used to fabricate the magnetic circuit 302 may be appropriate to the peak amplitude and frequency of the AMF. The material may be, but is not limited to, iron, powdered iron, assorted magnetic alloys in solid or laminated configurations and ferrites. The pole faces 104, 204, and 304 may be shaped and sized to further concentrate the flux produced in the treatment area. The pole faces 304 may be detachable. Different pole pieces having different sizes and shapes may be used, so that the treatment area and volume may be adjusted. When passing from one material to another, the lines of magnetic flux 312 travel in a direction normal to the plane of the interface plane. Thus, the face 304 may be shaped to influence the flux path through gap 333. The pole faces 304 may be detachable and may be chosen to extend the magnetic circuit 302 as much as possible, to minimize gap the 333 while leaving sufficient space to receive that portion of the patient being treated.

Figure 6:
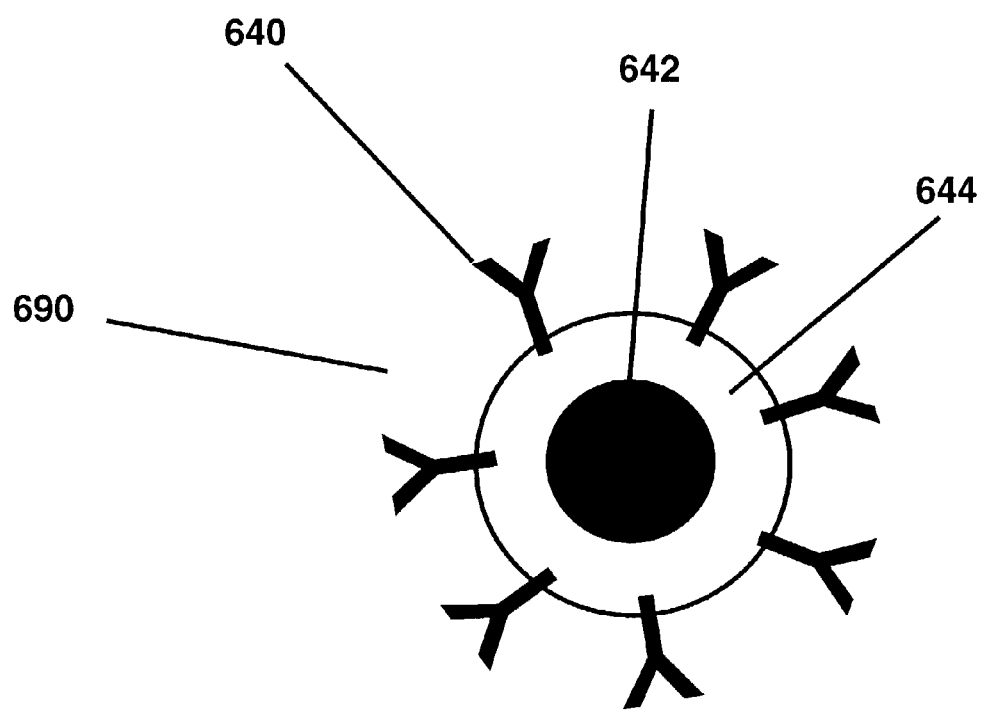
FIG. 6 schematically illustrates a thermotherapeutic bioprobe configuration according to an embodiment of the present invention.

FIG. 6 discloses a bioprobe configuration according to an embodiment of the present invention. A spherical shaped bioprobe 690, having a magnetic particle 642 at its center, is shown. The magnetic particle 642 may be covered with a coating 644. At least one targeting ligand 640, such as, but not limited to, an antibody, may be located on an exterior portion of the bioprobe 690. The targeting ligand 640 may be selected to seek out and bond with a particular type of diseased or cancerous cell. Heat is generated when the magnetic particle 642 of the bioprobe 690 is subjected to the AMF. In a general sense, this heat represents an energy loss as the magnetic properties of the material are forced to oscillate in response to the applied alternating magnetic field. The amount of heat generated per cycle of magnetic field and the mechanism responsible for the energy loss depend on the specific characteristics of both the magnetic material of the particle 642 and the magnetic field. The magnetic particle 642 heats to a unique temperature, known as the Curie temperature, when subjected to the AMF. The Curie temperature is the temperature of the reversible ferromagnetic to paramagnetic transition of the magnetic material. Below this temperature, the magnetic material heats in an applied AMF. However, above the Curie temperature, the magnetic material becomes paramagnetic and its magnetic domains become unresponsive to the AMF. Thus, the material does not generate heat when exposed to the AMF above the Curie temperature. As the material cools to a temperature below the Curie temperature, it recovers its magnetic properties and resumes heating, as long as the AMF remains present. This cycle may be repeated continuously during exposure to the AMF. Thus, magnetic materials are able to self-regulate the temperature of heating. The temperature to which the particle 642 heats is dependent upon the magnetic properties of the material, characteristics of the magnetic field, and the cooling capacity of the diseased tissue (tumor) site 214. Selection of the magnetic material and AMF characteristics may be tailored to optimize treatment efficacy of a particular tissue type. In an embodiment of the present invention, the magnetic material may be selected to possess a Curie temperature between 40° C. and 150° C.

The magnetic attributes of ferromagnets, ferrites (ferrimagnets), and superparamagnets are determined by an ensemble of interacting magnetic moments in a crystalline structure. The magnetic moments of ferromagnets are parallel and equal in magnitude, giving the material a net magnetization, or net magnetization vector. By contrast, ferrites are ferrimagnetic, where adjacent magnetic moments are parallel in direction and unequal in magnitude, yielding a net magnetization in ferrimagnetic coupling. Superparamagnets possess clusters or collections of atomic magnetic moments that are either ferromagnetic or ferrimagnetic, however there may be no particular relationship in the orientation of the moments among several clusters. Thus, a superparamagnetic material may possess a net magnetic moment.

A magnetic domain may be defined as an area of locally saturated magnetization, and the magnetic domain boundary thickness, or the distance separating adjacent magnetic domains, may be about 100 nm. Thus, magnetic particles (ferromagnetic or ferrimagnetic) possessing a dimension smaller than 250 nm, and preferably less than about 100 nm, are single domain magnetic particles, where each particle is a magnetic dipole.

The mechanisms responsible for energy loss exhibited by single domain particles exposed to an alternating magnetic field are still not well understood, however a currently accepted description exists, which is included herein for clarity. When a single domain particle is exposed to an AMF, the whole magnetic dipole rotates in response to the field with a concomitant energy loss liberated as heat. This mechanism is often referred to as the Neél mechanism. The external magnetic forces required for this intrinsic change in magnetization depend upon the anisotropy energy of the magnetic domain, size, and shape of the single domain particle. Furthermore, it is currently accepted that there is a mechanical rotation of the entire single domain particle when exposed to an alternating magnetic field. This latter phenomenon, commonly called the Brownian mechanism, also contributes to the energy loss of a single domain particle, and is proportional to the viscosity of the material surrounding the particle. Thus, the coating 644 may enhance the heating properties of the bioprobe 690, particularly if the coating is a polymer.

The heating mechanism responsible for the energy loss experienced by a single domain particle in an AMF can be clearly distinguished from the hysteresis heating of larger, or multidomain magnetic particles. Single domain particles of a given composition can produce substantially more heat per unit mass than multi-domain particles that are 1000 times larger (multi domain particles). The heating mechanism exhibited by single domain particles may be optimized to produce superior heating properties over larger particles for disease treatment. The amount of heat delivered to a cell may be tailored by controlling both the particle size and coating variation, as well as characteristics of the magnetic field, thereby providing a range of possible bioprobe compositions designed for tissue-specific treatments.

Many aspects of the magnetic particle 642, such as material composition, size, and shape, directly affect heating properties. Many of these characteristics may be designed simultaneously to tailor the heating properties for a particular set of conditions found within a tissue type. For example, first considering the magnetic particle 642, the most desirable size range depends upon the particular application and on the material(s) comprising the magnetic particle 642.

The size of the magnetic particle 642 determines the total size of the bioprobe 690. Bioprobes 690 that are to be injected may be spherical and may be required to have a long residence time in the bloodstream, i.e., avoid sequestration by the liver and other non-targeted organs. The bioprobe 690 may be successful in avoiding sequestration if its total diameter is less than about 30 nm. If the bioprobe 690 contains a magnetite ($Fe_3O_4$) particle 642, then a preferred diameter of the magnetic particle 642 may be between about 8 nm and about 20 nm. In this case, the bioprobes 690 may be sufficiently small to evade the liver, and yet the magnetic particle 642 still retains a sufficient magnetic moment for heating. Magnetite particles larger than about 8 nm generally tend to be ferrimagnetic and thus appropriate for disease treatment. If other elements, such as cobalt, are added to the magnetite, this size range can be smaller. This results directly from the fact that cobalt generally possesses a larger magnetic moment than magnetite, which contributes to the overall magnetic moment of the cobalt-containing magnetic particle 642. In general, the preferred size of the bioprobe 690 may be about 0.1 nm to about 250 nm, depending upon the disease indication and bioprobe composition.

While determining the size of the magnetic particle 642, its material composition may be determined, based on the particular targeted tissue. Because the self-limiting temperature of a magnetic material, or the Curie temperature, is directly related to the material composition, as is the total heat delivered, magnetic particle compositions may be tuned to different tissue types. This may be required because each tissue type, given its composition and location within the body, possesses unique heating and cooling capacities. For example, a tumor located within a region that is poorly supplied by blood and located within a relatively insulating region may require a lower Curie temperature material than a tumor that is located near a major blood vessel. Thus, in addition to magnetite, particle compositions may contain elements such as cobalt, iron, rare earth metals, etc.

The presence of the coating 644 and the composition of the coating material may form an integral part of the energy loss, and thus the heat produced, by the bioprobes 690. In addition, the coating 644 surrounding the particles may serve additional purposes. Its most important role may be to provide a biocompatible layer separating the magnetic material from the immunologic defenses in a patient, thereby controlling the residence time of the particles in the blood or tissue fluids.

For example, this control of residence time allows one to choose targeting ligands 640 that are best suited for a particular tissue type. In addition, the coating 644 may serve to protect the patient from potentially toxic elements in the magnetic particle 642. A second function of the coating materials may be the prevention of particle aggregation, as the bioprobes 690 may be suspended in a fluid. It may be also be advantageous to coat the magnetic particle 642 with a biocompatible coating 644 that is biodegradable. In such an application, both the coating 644 and the magnetic particle 642 may be digested and absorbed by the body.

Suitable materials for the coating 644 include synthetic and biological polymers, copolymers and polymer blends, and inorganic materials. Polymer materials may include various combinations of polymers of acrylates, siloxanes, styrenes, acetates, akylene glycols, alkylenes, alkylene oxides, parylenes, lactic acid, and glycolic acid. Further suitable coating materials include a hydrogel polymer, a histidine-containing polymer, and a combination of a hydrogel polymer and a histidine-containing polymer.

Coating materials may include combinations of biological materials such as a polysaccharide, a polyaminoacid, a protein, a lipid, a glycerol, and a fatty acid. Other biological materials for use as a coating material may be a heparin, heparin sulfate, chondroitin sulfate, chitin, chitosan, cellulose, dextran, alginate, starch, carbohydrate, and glycosaminoglycan. Proteins may include an extracellular matrix protein, proteoglycan, glycoprotein, albumin, peptide, and gelatin. These materials may also be used in combination with any suitable synthetic polymer material.

Inorganic coating materials may include any combination of a metal, a metal alloy, and a ceramic. Examples of ceramic materials may include a hydroxyapatite, silicon carbide, carboxylate, sulfonate, phosphate, ferrite, phosphonate, and oxides of Group IV elements of the Periodic Table of Elements. These materials may form a composite coating that also contains any biological or synthetic polymer. Where the magnetic particle 642 is formed from a magnetic material that is biocompatible, the surface of the particle itself operates as the biocompatible coating.

The coating material may also serve to facilitate transport of the bioprobe 690 into a cell, a process known as transfection. Such coating materials, known as transfection agents, include vectors, prions, polyaminoacids, cationic liposomes, amphiphiles, and non-liposomal lipids or any combination thereof. A suitable vector may be a plasmid, a virus, a phage, a viron, a viral coat. The bioprobe coating may be a composite of any combination of transfection agent with organic and inorganic materials, such that the particular combination may be tailored for a particular type of a diseased cell and a specific location within a patient's body.

To ensure that the bioprobe 690 selectively attaches to the diseased cells, an appropriate ligand 640 may be combined with the bioprobe 690. The association of a ligand or ligands with the bioprobes 690 allows for targeting of cancer markers on cells. The term ligand relates to compounds which may target molecules including, for example, proteins, peptides, antibodies, antibody fragments, saccharides, carbohydrates, glycans, cytokines, chemokines, nucleotides, lectins, lipids, receptors, steroids, neurotransmitters, Cluster Designation/Differentiation (CD) markers, and imprinted polymers and the like. The preferred protein ligands include, for example, cell surface proteins, membrane proteins, proteoglycans, glycoproteins, peptides and the like. The preferred nucleotide ligands include, for example, complete nucleotides, complimentary nucleotides, and nucleotide fragments. The preferred lipid ligands include, for example phospholipids, glycolipids, and the like. The ligand 640 may be covalently bonded to or physically interacted with the magnetic particle 642 or the coating 644. The ligand 640 may be bound covalently or by physical interaction directly to an uncoated portion of the magnetic particle 642. The ligand 640 may be bound covalently or by physical interaction directly to an uncoated portion of the magnetic particle 642 and partially covered by the coating 644. The ligand 640 may be bound covalently or by physical interaction to a coated portion of the bioprobe 690. The ligand 640 may be intercalated to the coated portion of the bioprobe 690.

Covalent bonding may be achieved with a linker molecule. The term "linker molecule," as used herein, refers to an agent that targets particular functional groups on the ligand 640 and on the magnetic particle 642 or the coating 644, and thus forms a covalent link between any two of these. Examples of functional groups used in linking reactions include amines, sulfhydryls, carbohydrates, carboxyls, hydroxyls and the like. The linking agent may be a homobifunctional or heterobifunctional crosslinking reagent, for example, carbodiimides, sulfo-NHS esters linkers and the like. The linking agent may also be an aldehyde crosslinking reagent such as glutaraldehyde. The linking agent may be chosen to link the ligand 640 to the magnetic particle 642 or the coating 644 in a preferable orientation, specifically with the active region of the ligand 640 available for targeting. Physical interaction does not require the linking molecule and the ligand 640 be bound directly to the magnetic particle 642 or to the coating 644 by non-covalent means such as, for example, absorption, adsorption, or intercalation.

Figure 7:
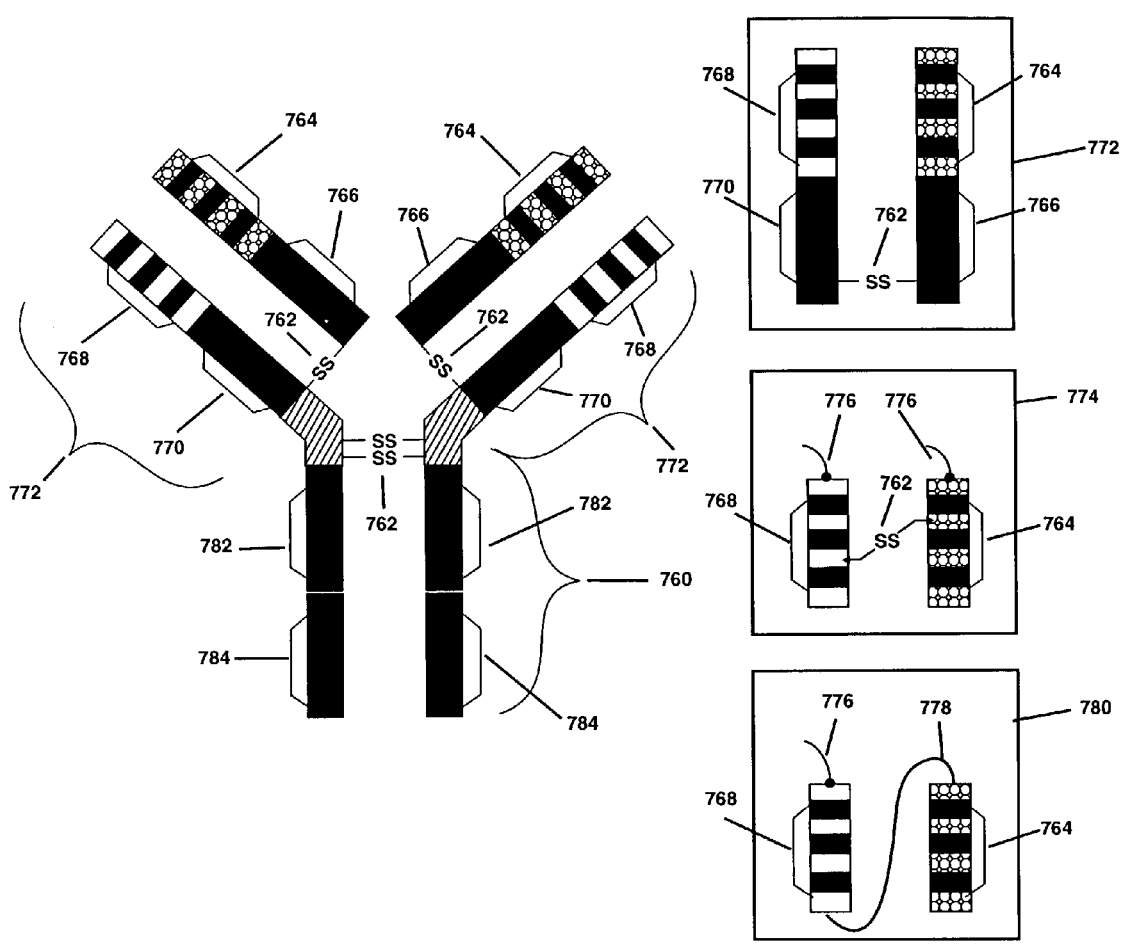
FIG. 7 schematically illustrates a disease specific targeting ligand component of a bioprobe according to an embodiment of the present invention.

FIG. 7 schematically shows an example of a ligand that may be used with an embodiment of the present invention. The ligand may be an antibody having a fragment crystallization (Fc) region 760 and fragment antigen binding (Fab) regions 772. The Fab regions 772 may be the antigen binding regions of the antibody that include a variable light region 764 and a constant light region 766 along with a variable heavy region 768 and a constant heavy region 770. Biological activity of antibodies may be determined to a large extent by the Fc region 760 of the antibody molecule. The Fc region may include complement activation constant heavy chains 782 and macrophage binding constant heavy chains 784. The Fc region 760 and Fab regions 772 may be connected by several disulfide linkages 762. Ligands that do not include the Fc region 760 may be preferable in order to avoid immunogenic response. Examples of these ligands may include antibody fragments such as, fragment antigen binding fragments (Fabs) 772, disulfide-stabilized variable region fragments (dsFVs) 774, single chain variable region fragments (scFVs) 780, recombinant single chain antibody fragments, and peptides.

An antigen binding fragment (Fab) 772 may include a single Fab region 772 of an antibody. A single Fab region may include a variable light 764 and a constant light region 766 bound to a variable heavy 768 and a constant heavy region 770 by a disulfide bond 762.

A disulfide-stabilized variable region fragment (dsFV) 774 may include a variable heavy region 768 and a variable light region 764 of antibody joined by a disulfide bond. A leader sequence 776, which may be a peptide, may be linked to the variable light 764 and variable heavy regions 768.

A single chain variable region fragment (scFV) 780 may include a variable heavy region 768 and variable light region 764 of antibody joined by a linker peptide 778. A leader sequence 776 may be linked to the variable heavy region 768.

A preferred ligand embodiment may include, for example, polyclonal antibodies, monoclonal antibodies, chimeric antibodies, humanized antibodies, human antibodies, recombinant antibodies, bispecific antibodies, antibody fragments, scFVs 780, Fabs 772, dsFVs 774, recombinant single chain antibody fragments, peptides, and the like. Bispecific antibodies are non-natural antibodies that bind two different epitopes that are typically chosen on two different antigens. A bispecific antibody is typically comprised of two different fragment antigen binding regions (Fabs) 772. A bispecific antibody may be formed by cleaving an antibody into two halves by cleaving the disulfide bonds 762 in the Fc region 782 only. Two antibody halves with different Fab regions 772 are then combined to form a bispecific antibody with the typical "Y" structure. One or more ligands can be present in the bioprobe formulation. Antibodies of virtually any origin may be used according to this embodiment, provided they bind the cancer marker target, although human, chimeric, and humanized antibodies may aid in avoiding the patient's immunogenic response.

In another embodiment, the ligand 640 may be designed to target a specific cancer cell marker or markers. The particular cancer cell marker and ligand(s) 640 may be specific to, but not limited to, the type and location of the cancer such as, for example, tumors, metastatic cancer, minimal residual disease and the like. The ligand(s) 640 may have an affinity for the cancer marker or markers of interest. The cancer marker or markers may be selected such that they represent a viable target on the cancer cells of interest. The preferred cancer marker may be expressed on the surface of the cancer cells and is preferably present in very low amounts or not at all in normal cells. The preferred cancer marker may not be readily shed from the surface, or if shed, the ligand on the bioprobe may recognize a particular epitope of the marker that remains on the cell surface.

Figure 8:
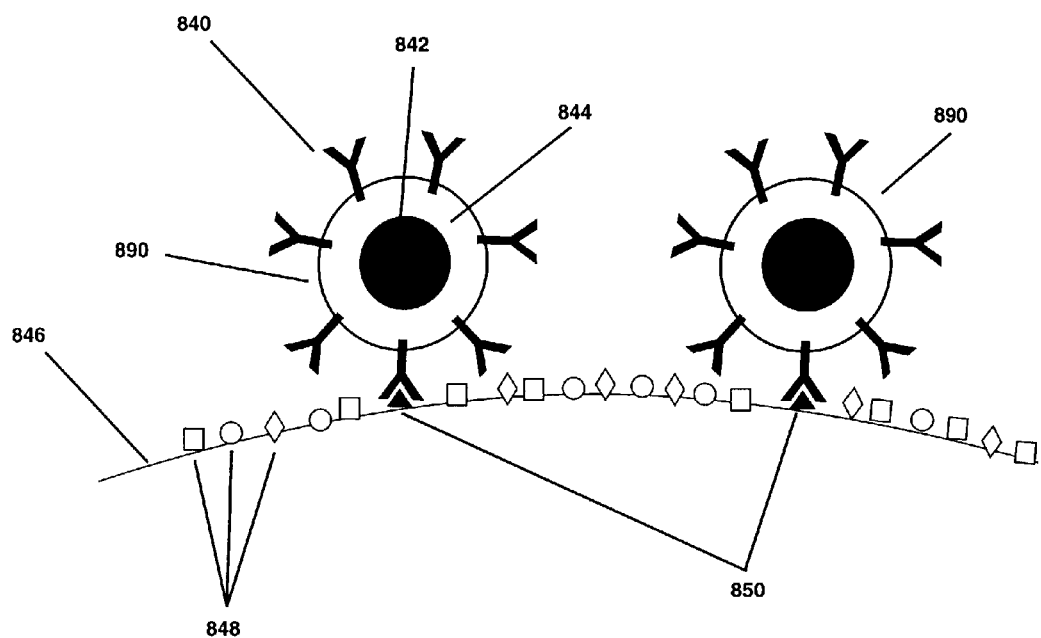
FIG. 8 schematically illustrates disease specific bioprobes bound to a disease cell surface according to an embodiment of the present invention.

FIG. 8 discloses an embodiment of the present invention wherein the bioprobes 890 include a magnetic particle 842 and a coating material 844 and are bound to the cancer cell surface (wall) 846 by the ligand 840. The cell wall 846 may express several types of chemical species 848 and 850 that may serve as markers. The specificity of the bioprobes 890 may be represented by attachment to the targeted cell marker 850 over the many other markers or molecules 848 on the cell surface 846. One or more bioprobes may be attached to the cell surface 846 via the ligand 840. The ligands 840 may be adapted and the bioprobes 890 may be designed such that the bioprobes 890 remain on the cell surface 846 or they may be internalized into the cell. Once bound to the cell surface 846, the magnetic particle 842 of the bioprobe 890 heats in response to the AMF. The heat may emanate through the coating material 844 or through interstitial regions via convection, conduction, radiation, or any combination of these heat transfer mechanisms to the cell surface 846. The heated cell surface 846 becomes damaged, preferably in a manner that causes irreparable damage to the cell. When a bioprobe(s) 890 becomes internalized within the cell, the bioprobe heats the cell internally via convection, conduction, radiation, or any combination of these heat transfer mechanisms. When a sufficient amount of heat is transferred by the bioprobes 890 to the cell, the cell dies by necrosis, apoptosis or another mechanism.

The choice of a cancer marker (antigen) 850 may be important to therapy utilizing bioprobes. For breast cancer, a specific marker or markers may be chosen from cell surface markers such as, for example, members of the MUC-type mucin family, an epithelial growth factor (EGFR) receptor, a carcinoembryonic antigen (CEA), a human carcinoma antigen, a vascular endothelial growth factor (VEGF) antigen, a melanoma antigen (MAGE) gene, family antigen, a T/Tn antigen, a hormone receptor, growth factor receptors, a cluster designation/differentiation (CD) antigen, a tumor suppressor gene, a cell cycle regulator, an oncogene, an oncogene receptor, a proliferation marker, an adhesion molecule, a proteinase involved in degradation of extracellular matrix, a malignant transformation related factor, an apoptosis related factor, a human carcinoma antigen, glycoprotein antigens and DF3, 4F2 and MGFM antigens.

In another embodiment of the invention, a bioprobe may include ligand(s) targeting the MUC-1 receptor of the mucin family. In yet another embodiment, a bioprobe has ligand(s) targeting at least one of the EGFR family such as Her-1, Her-2, Her-3 and Her-4. MUC-1 (Human epithelial mucin, CD277), is a high molecular weight, transmembrane mucin glycoprotein expressed by most glandular and epithelial cell lineages. In addition, MUC-1 has a large extracellular domain, portions of which may be shed into the bloodstream. MUC-1 may have a protective role, as its extracellular domain forms elongated rigid structures extending above other molecules on the cell. MUC-1 also plays a role in cell-cell and cell-substrate adhesion. MUC-1 is highly expressed in many human adenocarcinomas, including 80% of breast cancers, and is associated with poor prognosis.

Mucin (MUC-1 and MUC-2) expression is associated with tumor invasiveness. MUC-1 and MUC-2 expression is associated with invasive ductive carcinoma of the breast. MUC-1 is also present at high levels on many mylomas. Different tissues/cells produce differing glycoforms of MUC-1. Glycosylation of MUC-1 in malignant cells is often altered compared to normal tissue. MUC-1 is considered a truly tumor specific antigen, although it is also found on normal cells, its aberrant glycosylation on tumors creates new epitopes for targeting. The extracellular domain of MUC-1 may be shed into the blood stream The ligand may target the unshed remainder of the MUC-1 expressed on the cell surface.

Overexpression of growth factor receptors such as the EGFR family is indicated in tumors and has been associated with increased cell resistance to the cytotoxic effects of macrophages and cytotoxic factors, such as TNF (tumor necrosis factor), which can lead to tumor growth. The protein encoded by the Her-1/neu gene is a 170,000 Dalton protein, referred to as Her-1. The protein encoded by the Her-2/neu gene is a 185,000 Dalton protein referred to as Her-2. Both proteins have an intracellular domain, a transmembrane domain that includes two cysteine-rich repeat clusters, and an intracellular kinase domain. The extracellular domain of Her-2 may be shed into the bloodstream. Thus, the ligand may target the unshed remainder of the Her-2 expressed on the surface of the cell.

A method of administering the bioprobes 890 to the desired area for treatment and the dosage may depend upon, but is not limited to, the type and location of the cancer. The size range of the bioprobes 890 allows for microfiltration for sterilization. An administration method may be, for example, wash, lavage, as a rinse with sponge, or other surgical cloth after surgery, or intravascular injection, intravenous injection, intraperitoneal injection, subcutaneous injection, and intramuscular injection. The bioprobes 890 may be formulated in an injectable format (suspension, emulsion) in a medium such as, for example, water, saline, Ringer's solution, dextrose, albumin solution, and oils. Delivery of the bioprobes 890 to the target site may be assisted by an applied static magnetic field due to the magnetic nature of the bioprobes. Assisted delivery may depend on the location of the targeted cancer. The bioprobes may also be delivered to the patient using other methods. For example, the bioprobes may be administered to the patient orally, or may be administered rectally.

EXAMPLES

Having generally described the invention, a more complete understanding thereof may be obtained by reference to the following examples that are provided for purposes of illustration only and do not limit the invention.

Example 1

Identify Ferromagnetic Particles with Proper Curie Temperatures

For magnetic materials, the saturation magnetization ($4\pi M_s$) and the Curie temperatures ($T_c$) depend on the material composition. The Curie temperature of the material may lie in the range 40° C.–150° C., although it may also lie outside this range. For example, manganese alloys of the general formula $RMn_2X$, where R is a rare earth, such as La, Ce, Pr, or Nb, and X is either Ge or Si, exhibit $T_c$'s of 30–60° C. and may be used in bioprobes. Other oxides of ferrite, garnets, and spinels may be used as bioprobes. For example, substituting (doping) Gd and Al for Fe of $Y_3Fe_5O_{12}$ garnets provides control of both $T_c$ and $4\pi M_s$. These types of ferromagnetic media are commercially available from, for example, TRAK Ceramics, Hagerstown, Md.; Ceramic Magnetics, Fairfield, N.J.; and TMC Magnetics, Pine Brook, N.J. Sub-micron size particles may be produced through ball milling, solution-precipitation, or sol-gel processing of these materials.

The heating profile (temperature versus time) of the magnetic material may be determined under a variety of model conditions, for example, as suspensions in water, within cell culture media, agar gel, etc.

In general, a fundamental frequency of several MHz is effective for inductive heating. At such frequencies, however, tissue heating may be problematic. Another frequency range, which results in less tissue heating, is 100 kHz to 500 kHz.

Tissue heating places limitations on the practical amplitude of the magnetic field. A preferred range may be from 100 to 200 Oersteds (Oe), using a constant waveform generator. Difficulties may arise in achieving desired particle heating with many materials when the field falls in this range. The field conditions may also be inadequate because the number of bioprobes attaching to the targeted cells may often be unknown and/or limited by the specifics of cellular biology. The limitation may be overcome by using a pulsed generator and setting the field conditions, field amplitude and pulse characteristics, to levels that heats the bioprobes sufficiently to kill targeted cells without excessive peripheral tissue heating. Thus, under pulsed conditions, peak magnetic fields of up to a few thousand Oersteds (Oe) may be used.

Example 2

Synthesis of Bio-Compatible Coating

The bioprobe particles selected during EXAMPLE 1 may be coated with a biocompatible polymer according to a following embodiment of the procedure. Poly (methacrylic acid-co-hydroxyethylmethacrylate) as a biocompatible coating material for bioprobes may be synthesized from methacrylic acid and hydroxyethyl methacrylate using free-radical polymerization in the presence of the magnetic particles. To avoid aggregation of the magnetic nanometer sized particles during polymerization, the polymerization may be carried out in a microemulsion environment consisting of water/toluene/sodium bis-2-ethylhexyl sulfosuccinate. The sodium bis-2-ethylhexyl sulfosuccinate acts as an ionic surfactant to make a stabilizing layer around the magnetic particles. Methacrylic acid ($1.45 \times 10^{-2}$ moles), hydroxyethylmethacrylate ($5.38 \times 10^{-4}$ moles), N,N'-methylene bisacrylamide ($8.12 \times 10^{-5}$ moles), and 2,2'-azobisbutyronitrile ($7.62 \times 10^{-5}$ moles) are added to a mixture of water/toluene/bis-2-ethylhexyl sulfosuccinate ($0.38/0.47/5.1 \times 10^{-2}$ moles) with magnetic particles. The polymerization may be carried out at 55° C. for several hours under nitrogen. Coated bioprobe particles may then be recovered by precipitation in an excess of acetone/ethanol followed by several washings. The coated bioprobe particles may be kept in vacuum overnight to remove residual monomers.

Example 3

Attachment of the Antibodies to the Particles

The attachment of the antibodies to the coated magnetic particles may be accomplished by use of a small "linker" molecule with differentiated terminals that permit covalent antibody attachment to the biocompatible polymer coating. Attachment occurs in the Fc region using the electrophilic C-terminal residue of the antibody to react with the nucleophilic portion of the linker. The other terminus of the linker may be activated by UV photolysis. The photoactive end of the linker may react with the polymer coating. Conjugation of the antibodies to the nanoparticles using this technique may proceed in the following manner. The antibody may be covalently conjugated to 4-[p-azidosalicylamido]butylamine (ASBA) using 1-ethyl-3-(3-dimethylaminopropyl)-carbodiimide, EDC. The EDC may activate the C-terminal carboxyl function, making it susceptible to attack by the primary amino group of the ASBA. The antibody, covalently tethered to the linker, may be subjected to photolysis in the presence of the polymer-coated nanoparticles. On exposure to UV, the azido function on the linked ASBA may generate a nitrene in-situ that covalently inserts into the polymer coat yielding a nanoparticle that may be covalently bound to the antibody through the linker.

If the selected magnetic nanoparticles are not toxic and do not require polymer coating, the antibodies may be attached to the nanoparticles directly. The immunoglobulin G's may be cleaved at the disulfide linkages connecting the two portions of the antibody and purified by chromatography. The fragments, containing residual sulfhydryl groups, may be conjugated directly to the metal clusters forming coordinate covalent linkages.

Example 4

Efficacy of Bioprobes: In vitro Trials with MCF-7 Breast Cancer Cells

The bioprobes included 50 nm, $Fe_3O_4$ particles surrounded by a dextran shell, to which the monoclonal antibody (mAB) for Her-2 was covalently linked. The particles were suspended in cellular growth media including Modified Eagle's Medium (MEM) containing 10% fetal calf serum, insulin (10 µg/ml), fungizone, glutamine, penicillin, streptomycin, sodium pyruvate and non-essential amino acids, which was then added to cultures of MCF-7 cells. The MCF-7 cells represent an estrogen receptor-positive human breast carcinoma, and were grown on tissue culture inserts with a 10 mm diameter possessing porous frits with pore sizes of 0.02 or 0.2 µm.

The alternating magnetic field source was an industrial 3.5 kW variable duty radio-frequency generator with a frequency of 740 kHz and time-averaged field amplitude of 500 Oe (peak field amplitude, 1300 Oe). The generator produced pulses with a length of 4.174 ms, at a pulse repetition rate of 121 Hz, to give a duty cycle of 50.6%. The generator provided power to a 14-mm (inner diameter), 5-turn copper solenoid coil into which sample containers were inserted. The average temperature of the media in all samples monitored in situ using silicon dioxide temperature probes resistant to electromagnetic (EM) fields (obtained from FISO Technologies Inc., Ste-Foy, Quebec, Canada).

A series of water bath tests was conducted to determine the hyperthermia tolerance of the cell cultures. The purpose of these tests was to obtain "positive control" data on the effects of hyperthermia on the cancer cell cultures and to aid in the interpretation of experiments using the bioprobe system. Exposing cellular culture media to an alternating magnetic field, without the presence of the bioprobes, may cause some tissue heating. Such magnetic induction heating is determined by the frequency and field strength of the magnetic field. Thus, to avoid overheating the media with the applied magnetic field, water bath tests were conducted to provide threshold limits of magnetic induction heating of the media containing cells not receiving the treatment. Table 1 lists results of cell death fraction as a function of exposed temperature and exposure time. The MCF-7 cell line is shown to be unaffected by heat exposure to 42° C. for 30 minutes. Thus, for all in vitro experiments, the magnetic field strengths were fixed at levels where the average temperature of the cellular growth media (containing no cells or magnetic fluid) remained at or below 42° C.

TABLE 1

| Result of water bath tests with MCF-7 cells | | |
|---|---|---|
| Temperature (° C.) | Time of exposure (min.) | % dead cells |
| 37* | N/A | 4 |
| 42 | 30 | 4 |
| 43 | 15 | 5 |
| 46 | 5 | 92 |

*Represents a control cell culture sample not placed into water bath.

Cells intended for treatment were combined with bioprobes containing the Her-2 antibody and incubated for 8 minutes at 20° C., followed by three rinses with growth media, to remove unattached bioprobes. The cell cultures were analyzed before and 6 hours after the 20-minute treatments with the alternating magnetic field (AMF). The fraction of dead cells for the targeted sample (T1) and control samples (C1–C3) are presented in Table 2. In the targeted sample, 91%±5% (n=7) of the MCF-7 cells were killed. Of the cells killed, about 70% cells were be lysed by the treatment, as measured by spectrophotometric analysis of cytoplasmic lactate dehydrogenase (LDH), an enzyme produced by living cells. The remaining approximately 20% underwent apoptosis, as measured using a commercial fluorescent apoptosis-staining assay. The kill rates for the targeted cells are significantly higher than baseline death and apoptotic rates of 4%±1% in all controls (Table 2). Control groups include: 1) cells receiving no exposure to either the AMF or bioprobes (Sample C1); 2) cells exposed to the bioprobes alone (Sample C2); and 3) cells exposed to the AMF alone (Sample C3). Similar baseline deaths of all controls confirm that neither the AMF alone, nor only the presence of the bioprobes, is toxic to the cells. Higher than normal cell death occurs only when the AMF is applied after the bioprobes have attached to a cell.

TABLE 2

| IN VITRO RESULTS WITH MCF-7 CELLS | | |
|---|---|---|
| SAMPLE | TREATMENT | % DEAD CELLS (N = 7) |
| C1 | NO BIOPROBES, NO AMF | 4 ± 1 |
| C2 | BIOPROBES, NO AMF | 5 ± 1 |
| C3 | NO BIOPROBES; AMF | 4 ± 1 |
| T1 | BIOPROBES WITH AMF | 91 ± 5 |

Example 5

Selectivity of Bioprobes: In vitro Trials with SK-CO-1 Colon Cancer Cells

For the in vitro studies, the MCF-7 human breast cancer cells were chosen because their Her-2 expression was sufficient for detection, but was not expressed in extraordinarily high amounts as is the case with the more aggressive MDA-MB-231 (human breast carcinoma cells known to significantly over express Her-2) cell line. As a control, cultures of SK-CO-1 cells (human colon adenocarcinoma cells known to be Her-2 negative) were chosen to provide a reasonable model to challenge the effectiveness and selectivity of the bioprobe system.

To investigate the selectivity of the bioprobes, SK-CO-1 human colon cancer cells known to be Her-2 negative were treated in the same manner. For this group, rates of apoptosis were 13% for cells treated with an alternating magnetic field (AMF) and bioprobes, 18% for cells receiving no AMF and no bioprobes (represents normal death rate), 10% for cells exposed only to an AMF, and 8% for cells exposed to only bioprobes. These results are summarized in Table 3. Thus, no significant differences were seen in the death rates of SK-CO-1 cells when used with any or all components of the invention, demonstrating selective tumoricidal activity for the MCF-7 breast cells.

TABLE 3

IN VITRO RESULTS WITH SK-CO-1 CELLS

| SAMPLE | TREATMENT | % DEAD CELLS |
|---|---|---|
| SK-CO-1 | NO BIOPROBES, NO AMF | 18 |
| SK-CO-1 | BIOPROBES, NO AMF | 8 |
| SK-CO-1 | NO BIOPROBES; AMF | 13 |
| T1 (MCF-7) | BIOPROBES WITH AMF | 91 ± 5 (N = 7) |

Example 6

Bioprobe Targeting MUC-1 Receptor in Breast Cancer

The target on the breast cancer cells may be MUC-1 (Human epithelial mucin, CD277) marker. MUC-1 is highly expressed in many human adenocarcinomas including 80% of breast cancers and is associated with poor prognosis. The ligand on the bioprobe may be an antibody which targets the MUC-1 receptor. Commercial monoclonal mouse anti-human MUC-1 antibodies may be used in preliminary in vitro studies, from such sources as Chemicon International, Temecula, Calif.; and Zymed Laboratories, South San Francisco, Calif. The MUC-1 bioprobes may be formed from 50 nm dextran coated $Fe_3O_4$ particles. The mouse anti-human MUC-1 is a whole antibody and the Fc portion may be linked to the magnetic particle or the dextran coating through several different techniques. A linking agent, such as $BS^3$, available from Pierce, Rockford, Ill., may be used with silanization or the antibody may be biotinylated and attached to a streptavidin-containing, 50 nm dextran coated particle.

In vitro studies demonstrate dose response and proof of killing of cancer cells above the level of the controls. The targeted bioprobes may be further refined by producing Fab and scFV fragments of a monoclonal mouse anti-human MUC-1 antibody, fragments from an antibody library, humanization of the antibody, or production of peptides. Antibodies, fragments, and peptides may be engineered with altered properties such as antigen binding affinity, molecular architecture, and specific receptor epitope targeting to enhance the tumor targeting and potency. The use of fragments, humanized antibody, or peptides creates a ligand that avoids immunogenic response in humans.

The MUC-1 receptor is considered a truly tumor specific antigen because although it is on normal cells, its aberrant glycosylation on tumors creates new epitopes for targeting. The extracellular domain of MUC-1 is shed into the blood stream which makes the selection of the targeting ligand a very important component in this example. The MUC-1 targeting ligand may be selected to avoid the shed portion of the extracellular domain of MUC-1 in the bloodstream. This may result in reducing delivery problems and dilution of the treatment by bioprobes binding to the shed receptor. The MUC-1 targeting ligand recognizes an epitope of MUC-1 which remains on the cancer cell after a portion of the extracellular domain is shed. This choice of ligand allows the bioprobe to specifically and selectively target breast cancer cells.

Example 7

Temperature Monitoring During Treatment

In a treatment cycle, the bioprobes 210 may be exposed to and become attached to metastatic cells in the treatment area. Pole pieces 204 may be chosen to provide treatment in a selected treatment area, for example, approximately 6 inches in diameter. The patient 105 is typically placed on the treatment bed 206, and the bed controller 108 is typically adjusted to place the targeted tissue at the region of maximum field strength between the poles 204. The pulse width, duty cycle, and peak amplitude of the AMF and the treatment time may be adjusted. Several temperature probes, for example, four temperature probes, may be inserted into the treatment volume. One probe may be located centrally and the other three may be inserted into tissues, within the treatment area that are heated by the AMF. As the tissue heats under the applied AMF, the temperature probes 354 send data to the probe monitor 352. The monitor sends the temperature data via the feedback loop 324 to the RF generator controller 356. Monitoring may be continuous, for example at a data rate of 10 samples per second and the duty of the RF generator 318 may be adjusted once per second based on individual, 10 sample averages from each probe. If none of the probes 354 sense a temperature greater than the preset limit, the RF generator 318 may be permitted to operate at the original settings. If one or more of the probes 354 senses a temperature over the preset threshold, the controller 356 may send a command to reduce at least one of the duty cycle, the PRF, the magnitude of the magnetic field. This process continues until the treatment is completed.

While the above description of the invention has been presented in terms of a human patient, it will be appreciated that the invention may also be applicable to treating cancers in other mammals.

As noted above, the present invention is applicable to a magnetic material composition, a system and method of thermotherapy for the treatment of cancers. The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

What is claimed is:

1. A magnetic material composition, comprising:
   a) a single domain magnetic particle capable of being heated by Neél relaxation in response to an alternating magnetic field;
   b) a biocompatible coating material for the particle; and
   c) a ligand selective to at least one cancer marker on a cell in cancer tissue, the ligand being i) bound to an uncoated portion of the particle, ii) bound to a coated portion of the particle, iii) bound to the particle and partially covered by the coating, or iv) intercalated into the coating.

2. A magnetic particle composition of claim 1, wherein the particle has a size of no more than 250 nm in at least one dimension.

3. A magnetic material composition of claim 1, wherein the particle, the coating and the ligand are suspended in a biologically compatible fluid.

4. A magnetic material composition of claim 1, wherein the magnetic particle has a Curie temperature in the range of about 40° C. to about 150° C.

5. A magnetic material composition of claim 1, wherein the magnetic particle is formed of a biocompatible material, the surface of the magnetic particle forming the biocompatible coating.

6. A magnetic material composition of claim 1, wherein the biocompatible coating material is one of an organic material, an inorganic material, and a combination of an inorganic material and an organic material.

7. A magnetic material composition of claim 6, wherein the organic material is at least one of a synthetic material and a biological material.

8. A magnetic material composition of claim 7, wherein the synthetic material is a polymer, a copolymer, or a combination thereof.

9. A magnetic material composition of claim 7, wherein the synthetic material is selected from the group consisting of i) a polymer, ii) a copolymer, and iii) a polymer blend formed from a polymer based on at least one of acrylates, styrenes, acetates, alkylene glycols, alkylenes, alkylene oxides, parylene, lactic acid, and glycolic acid.

10. A magnetic material composition of claim 7, wherein the synthetic material is selected from the group consisting of i) a hydrogel polymer, ii) a histidine-containing polymer, iii) a surfactant, and iv) a combination of at least one of i)–iii).

11. A magnetic material composition of claim 7, wherein the biological material is selected from the group consisting of i) a polysaccharide, ii) a polyaminoacid, iii) a protein, iv) a lipid, v) a glycerol, vi) a fatty acid, and vii) a combination including at least one of i)–vi).

12. A magnetic material composition of claim 11, wherein the polysaccharide is selected from the group consisting of a) a heparin, b) heparin sulfate, c) chondroitin sulfate, d) chitin, e) chitosan, f) cellulose, g) dextran, h) alginate, i) starch, j) saccharide, k) carbohydrate, l) glycosaminoglycan, and m) a combination of any of a)–l).

13. A magnetic material composition of claim 11, wherein the protein is selected from the group consisting of a) an extracellular matrix protein, b) proteoglycan, c) glycoprotein, d) albumin, e) peptide, f) gelatin, and g) a combination of any of a)–f).

14. A magnetic material composition of claim 6, wherein the inorganic material is selected from the group consisting of i) a metal, ii) a metal alloy, iii) a ceramic, iv) an oxide of a Group IV element, and v) a combination of any of i)–iv).

15. A magnetic material composition of claim 14, wherein the ceramic is selected from the group consisting of a) hydroxyapatite, b) silicon carbide, c) carboxylate, d) sulfonate, e) phosphate, f) ferrite, g) phosphonate, and h) a combination of any of a)–g).

16. A magnetic material composition of claim 7, wherein the biological material is a transfection agent to enhance uptake by cancer cells.

17. A magnetic material composition of claim 16, wherein the transfection agent is selected from the group consisting of i) a vector, ii) a prion, iii) a polyaminoacid, iv) a cationic liposome, v) an amphiphile, vi) a non-liposomal lipid, and vii) a combination of any of i)–vi).

18. A magnetic material composition according to claim 17, wherein the vector is selected from the group consisting of a) a plasmid, b) a virus, c) a phage, d) a viron, e) a viral coat, and f) a combination of any of a)–e).

19. A magnetic material composition of claim 17, wherein the polyaminoacid is a poly L-lysine.

20. A magnetic material composition of claim 7, wherein the synthetic material is a transfection agent.

21. A magnetic material composition of claim 20, wherein the transfection agent is selected from the group consisting of i) a non-lipid cationic polymer, ii) a dendrimer, iii) polyethyleneimine, and iv) a combination of any of i)–iii).

22. A magnetic material composition of claim 1, wherein the ligand is one of a molecule and a combination of molecules selective to at least one specific cancer marker.

23. A magnetic material composition of claim 22, wherein the molecule is selected from the group consisting of i) a saccharide, ii) a carbohydrate, iii) a glycan, iv) a protein, v) a peptide, vi) an antibody, vii) an antibody fragment, viii) a receptor, ix) a Cluster Designation/Differentiation (CD) marker, x) a cytokine, xi) a chemokine, xii) a nucleotide, xiii) a lipid, xiv) a steroid, xv) a neurotransmitter, xvi) a lectin, xvii) an imprinted polymer, xviii) an oncogene, xix) an oncogene receptor, and xx) a combination of any of i)–xix).

24. A magnetic material composition of claim 23, wherein the protein is selected from the group comprising a) a membrane protein, b) a proteoglycan, c) a cell surface protein, d) a glycoprotein, and e) a combination of any of a)–d).

25. A magnetic material composition of claim 23, wherein the antibody is selected from the group consisting of a) a polyclonal antibody, b) a monoclonal antibody, c) a chimeric antibody, d) a humanized antibody, e) a human antibody, f) a recombinant antibody, g) a bispecific antibody, h) an antibody fragment, i) a recombinant single chain antibody fragment and j) a combination of any of a–i).

26. A magnetic material composition of claim 23, wherein the nucleotide is selected from the group consisting of a) a complete nucleotide, b) a nucleotide fragment, c) a complementary nucleotide, and d) a combination of a)–c).

27. A magnetic material composition of claim 23, wherein the lipid includes a) a phospholipid, b) a glycolipid, or c) a combination of a) and b).

28. A magnetic material composition of claim 22, wherein the marker is specific to breast cancer.

29. A magnetic material composition of claim 27, wherein the marker is specific to a metastatic cancer related to breast cancer.

30. A magnetic material composition of claim 27, wherein the marker is specific to a primary cancer of the breast.

31. A magnetic material composition of claim 27, wherein the breast cancer-specific marker is selected from the group consisting of a) a member of the MUC-type mucin family, b) a member of the epidermal growth factor receptor (EGFR) family, c) a carcinoembryonic antigen (CEA), d) a MAGE (melanoma antigen) gene family antigen, e) a T/Tn antigen, f) a hormone receptor, g) a Cluster Designation/Differentiation (CD) antigen, h) a tumor suppressor gene, i) a cell cycle regulator, j) an oncogene, k) an oncogene receptor, l) a proliferation marker, m) an adhesion molecule, n) a proteinase involved in degradation of extracellular matrix, o) a malignant transformation related factor, p) an apoptosis related factor, q) a human carcinoma antigen, r) a member of the vascular endothelial growth factor (VEGF) receptor family, s) glycoprotein antigens, t) DF3 antigen, u) 4F2 antigen, v) MFGM antigen, and w) a combination of any of a) through v).

32. A magnetic material composition of claim 31, wherein the MUC-type mucin family marker is MUC-1.

33. A magnetic material composition of claim 31, wherein the EGFR is selected from the group consisting of at least one of Her-1, Her-2, Her-3, Her-4, and any combination thereof.

34. A magnetic material composition of claim 1, further comprising a linking agent linking between the ligand and the magnetic particle or between the ligand and the biocompatible coating material.

35. A magnetic material composition of claim 33, wherein the linking agent links to at least one of i) an amine group, ii) a sulfhydryl group, iii) a carbohydrate group, iv) a carboxyl group, v) a hydroxyl group, and vi) a combination of any of i)–v).

36. A magnetic material composition of claim 33, wherein the linking agent is comprised of at least one of i) homobifunctional crosslinkers, ii) heterobifunctional crosslinkers, iii) aldehydes, iv) homotrifunctional crosslinkers, v) heterotrifunctional crosslinkers, and a combination of any of i)–v).

37. A method for treating cancer in a patient, comprising:
a) administering the magnetic material composition of claim 1 to the patient; and
b) applying an alternating magnetic field to a region of the patient containing the cancer so as to inductively heat the magnetic material composition.

38. A method according to claim 37, further comprising inducing cancer cell death by the inductively heated magnetic material via necrosis or apoptosis.

39. A method according to claim 38, further comprising applying the alternating magnetic field to a region of the patient containing cancer tissue and to a region of the patient adjacent to the region containing the cancer tissue.

40. A method according to claim 37, further comprising applying a static magnetic field to a region of the patient containing cancer tissue to aid in localizing the magnetic material composition to the region containing the cancer tissue.

41. A method according to claim 37, further comprising monitoring at least one physical characteristic of at least one of cancer tissue and non-cancer tissue.

42. A method according to claim 41, wherein monitoring the at least one physical characteristic includes monitoring temperature.

43. A method according to claim 41, wherein monitoring the at least one physical characteristic includes monitoring tissue impedance.

44. A method according to claim 37, wherein the alternating magnetic field is applied to the patient over a treatment duration, and applying the alternating magnetic field includes pulsing the alternating magnetic field to have a pulse length less than the treatment duration.

45. A method according to claim 44, further comprising applying at least two pulses of alternating magnetic field to the patient.

46. A method according to claim 37, wherein administering the magnetic material composition includes injecting the magnetic material composition into the patient.

47. A method according to claim 37, further comprising a magnetic field generator that generates the alternating magnetic field, wherein the alternating magnetic field has a strength in the range of about 100 to about 2,000 Oe in the region of the patient containing the cancer.

48. A method according to claim 47, wherein the alternating magnetic field has a triangular waveform.

49. A method according to claim 37, wherein applying the alternating magnetic field includes modulating the alternating magnetic field.

50. A method according to claim 49, wherein modulating the magnetic field includes applying a modulation having one of a sinusoidal envelope, a triangular envelope, a square wave envelope, a trapezoidal envelope, and a sawtooth envelope.

51. A method for treating cancer in a patient, comprising:
a) administering to the patient a magnetic material composition of claim 1; and
b) applying an alternating magnetic field to a region of the patient containing the cancer such that the magnetic material composition inductively heats, wherein the alternating magnetic field is applied using a device comprising:
i) a magnetic generator having a core defining at least part of a magnetic circuit, two poles of the core defining a gap therebetween, a magnetic field passing between two poles, the gap being of sufficient size to receive a portion of the patient containing the cancer cells; and
ii) a power supply coupled to provide energy to the magnetic generator so that the magnetic field passing between the two poles alternates at a frequency in the range from about 1 kHz to about 1 GHz,
wherein the alternating magnetic field strength is in the range from about 10 Oe to about 10,000 Oe.

52. A method according to claim 51, wherein the magnetic material composition inductively heats to a sufficient temperature to induce cancer cell death.

53. A method according to claim 51, further comprising inducing cancer cell death by inductively heated magnetic material via necrosis, apoptosis or another mechanism.

54. A method according to claim 51, further comprising applying the alternating magnetic field to a region of the patient containing cancer tissue and to a region of the patient adjacent the region containing the cancer tissue.

55. A method according to claim 51, further comprising applying a static magnetic field to a region of the patient containing cancer tissue to aid in localizing the magnetic material composition to the region containing the cancer tissue.

56. A method according to claim 51, further comprising monitoring at least one physical characteristic of at least one of cancer tissue and non-cancer tissue while applying the alternating magnetic field.

57. A method according to claim 51, further comprising pulsing the alternating magnetic field while applying the alternating magnetic field.

58. A method according to claim 57, further comprising exposing the patient to at least two pulses of the alternating magnetic field while applying the alternating magnetic field.

* * * * *